(12) United States Patent
Kaplan

(10) Patent No.: US 7,415,883 B2
(45) Date of Patent: Aug. 26, 2008

(54) METHOD FOR PROTECTING RESONATING SENSORS AND OPEN PROTECTED RESONATING SENSORS

(75) Inventor: Shay Kaplan, Givat Elah (IL)

(73) Assignee: Zuli Holdings Ltd, Tel Aviv (IL)

( * ) Notice: Subject to any disclaimer, the term of this patent is extended or adjusted under 35 U.S.C. 154(b) by 669 days.

(21) Appl. No.: 10/876,763

(22) Filed: Jun. 28, 2004

(65) Prior Publication Data

US 2005/0288590 A1 Dec. 29, 2005

(51) Int. Cl.
*G01L 11/00* (2006.01)
(52) U.S. Cl. .............................. 73/703; 73/702; 73/570
(58) Field of Classification Search ........... 73/700–756, 73/570
See application file for complete search history.

(56) References Cited

U.S. PATENT DOCUMENTS

| | | | | |
|---|---|---|---|---|
| 5,557,971 | A * | 9/1996 | Uemura et al. ................. | 73/702 |
| 5,625,151 | A * | 4/1997 | Yamaguchi ................... | 73/716 |
| 5,989,190 | A * | 11/1999 | Kaplan ........................ | 600/438 |
| 6,142,954 | A * | 11/2000 | Anhauser et al. ............. | 600/556 |
| 7,134,341 | B2 * | 11/2006 | Girmonsky et al. ........... | 73/579 |
| 7,178,378 | B2 * | 2/2007 | Crawley et al. ............. | 73/24.06 |

* cited by examiner

*Primary Examiner*—Andre J. Allen
*Assistant Examiner*—Jermaine Jenkins
(74) *Attorney, Agent, or Firm*—AlphaPatent Associates Ltd.; Daniel J. Swirsky

(57) ABSTRACT

A protected resonating sensor may include at least one resonating sensor unit, each sensor unit has one or more vibratable members. The protected sensor includes at least one body of gel for protecting the vibratable member(s) of the sensor. The gel may be disposed on or attached to the sensor unit(s) covering the vibratable member(s) of the sensor unit(s). The gel may also be disposed in an open housing including one or more sensor units, and may cover vibratable members of different sensor units. The sensor unit may be any resonating sensor unit having a resonance frequency that depends on the value of a physical variable in a measurement environment. The protected sensor may also be attached to or included in or formed as part of any suitable device or sensor anchoring device and may also be implanted or inserted into a body or an organism. Methods are described for constructing the gel-protected sensor. The gel may have modified surface properties and may contain one or more drugs or therapeutic agents or other releasable substances. The gel may be formulated to retard or reduce diffusion of substances from the measurement environment into the gel and their deposition on the vibratable member(s).

61 Claims, 13 Drawing Sheets

METHOD FOR PROTECTING RESONATING SENSORS AND OPEN PROTECTED RESONATING SENSORS

FIELD OF THE INVENTION

The present invention relates generally to the field of resonating sensors in general and to methods for protecting resonating sensors from deposition of extraneous materials or tissues and protected resonating sensors in particular.

BACKGROUND OF THE INVENTION

Methods, devices and systems, using resonating sensors for determining the values of various physical parameters in a measurement environment are well known in the art. For example, methods systems and devices for using ultrasonically activated passive sensors for sensing and measuring the values of different physical parameters within a human body or in other environments and scientific and industrial applications, have been described. U.S. Pat. No. 5,619,997 to Kaplan, incorporated herein by reference in its entirety for all purposes, discloses a passive sensor system using ultrasonic energy.

An ultrasonic activation and detection system ultrasonically activates passive sensors having vibratable parts (such as vibratable beams or vibratable membranes) which sensor(s) may be implanted in a body or disposed in other environments, by directing a beam of ultrasound at the passive sensor or sensors. The activated passive sensor(s), or vibratable parts thereof, vibrate or resonate at a frequency that is a function of the value of the physical variable to be measured. The passive sensors thus absorb ultrasonic energy from the exciting ultrasonic beam at the frequency (or frequencies) of the exciting ultrasonic beam. The amplitude of vibration of a vibratable part of such a passive sensor is maximal when the frequency of the exciting ultrasonic beam is identical to the resonance frequency of the vibratable sensor part (such as, for example a vibratable membrane or a vibratable beam included in the passive sensor). The frequency (or frequencies) at which the passive sensor absorbs and/or emits energy may be detected by a suitable detector and used to determine the value of the physical parameter.

The physical parameters measurable with such passive ultrasonic sensors may include, but are not limited to, temperature, pressure, a concentration of a chemical species in the fluid or medium in which the sensor is immersed or disposed, and the like.

If the exciting ultrasonic beam is pulsed, the ultrasonic sensor may continue to vibrate after the excitation beam is turned off. The ultrasonic radiation emitted by the activated passive sensor after turning the exciting ultrasonic beam off may be detected and used to determine the value of the physical parameter of interest.

Since more than one physical variable may influence the vibration frequency of passive sensors, a correction may be needed in order to compensate for the effects of other physical parameters unrelated to the physical parameter which needs to be determined on the measured sensor vibration frequency. For example, if pressure is the physical parameter to be determined, changes in temperature may affect the vibration frequency of the sensor. U.S. Pat. Nos. 5,989,190 and 6,083,165 to Kaplan, both patents are incorporated herein by reference in their entirety for all purposes, disclose compensated sensor pairs and methods for their use for compensating for the effects of unrelated different physical variables on the determined value of another physical variable which is being determined. For example, such compensated sensor pairs, may be used for compensating for inaccuracies in pressure measurements due to temperature changes.

U.S. Pat. No. 6,331,163 to Kaplan, incorporated herein by reference in its entirety for all purposes, discloses implantable passive sensors having a protective coating, and various types of sensor positioners or sensor anchoring devices. Such sensors may be used, inter alia, for measuring intraluminal blood pressure by intraluminal implantation of the sensor(s).

Co-pending U.S. patent application Ser. No. 10/828,218 to Girmonski et al. entitled "METHODS AND DEVICES FOR DETERMINING THE RESONANCE FREQUENCY OF PASSIVE MECHANICAL RESONATORS" filed on Apr. 21, 2004, now issued as U.S. Pat. No. 7,134,341, incorporated herein by reference in its entirety for all purposes, discloses, inter alia, methods, resonating sensors and systems, that use a Doppler shift based method for determining the resonance frequency of passive resonators. The methods, sensors and systems, may be applied, inter alia, for sensing pressure or other physical parameters in a measurement environment, such as, but not limited to the in-vivo measurement of blood pressure within a part of a cardiovascular system.

While all the above examples are related to passive resonating ultrasonic sensors, many other types of resonating sensors including both active and passive sensors are known in the art for measurement of various different physical parameters. Such sensors have in common the use of one or more resonating vibratable structures or parts, such as, for example vibratable membranes or beams or the like, which may be passively or actively vibrated. The resonance frequency of the resonating structure of such sensors changes as a function of the physical variable to be determined and may be sensed or measured in various different ways and used to determine the value of the physical variable. Examples of such sensors are the active ultrasonic sensor disclosed in U.S. Pat. No. 6,461,301 to Smith. Additional sensor types are disclosed in U.S. Pat. No. 6,312,380 to Hoek et al.

A common problem when resonating sensors such as, but not limited to, the sensors described above are implanted within a living body is the deposition of tissue or other materials of biological origin on the sensor or on parts thereof. For example, various substances or living cells may attach to the surface of the resonating sensor or to various parts thereof and adjacent tissues may cause the deposition of a layer or film of material and/or cells, and/or tissues on the sensor's surface. The deposition of tissues or other biological materials on the vibratable part of the sensor, such as (but not limited to) the vibratable membrane of a passive (or active) resonating sensor may cause changes in the vibratable membrane (or the other vibratable part) resonance characteristics such as, inter alia, the resonance frequency, sensitivity to stress, and vibration amplitude of the vibratable membrane. Such changes may adversely affect the sensor's performance and the accuracy of the determination of the physical variable which is to be determined.

Similarly, when a resonating sensor is disposed within a fluid or gas or other medium or measurement environment which contains various substances (such as, for example, within a chemical reaction mixture in a reactor or in a measurement environment containing sprays or aerosols or the like), deposition of liquid or solid material or particles on the vibratable part of the resonating sensor may similarly affect the resonance characteristics of the vibratable part of the sensor with similar adverse effects on the sensor's performance.

BRIEF DESCRIPTION OF THE DRAWINGS

The invention is herein described, by way of example only, with reference to the accompanying drawings, in which like components are designated by like reference numerals, wherein.

SUMMARY OF THE INVENTION

Figure 1:
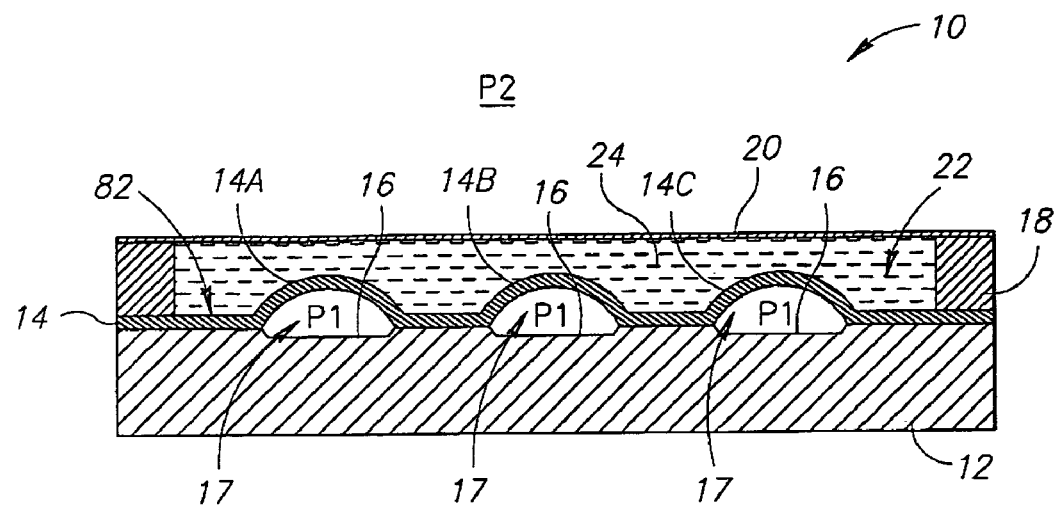
FIG. 1 is a schematic cross-sectional view illustrating a protected passive ultrasonic pressure sensor having multiple vibratable membranes, in accordance with an embodiment of the present invention.

There is therefore provided, in accordance with an embodiment of the present invention, a protected resonating sensor. The protected sensor includes one or more resonating sensor units. Each sensor unit of the resonating sensor unit(s) has at least one vibratable member having a resonance frequency that varies as a function of a physical variable in a measurement environment. The protected sensor also includes at least one body of gel in contact with the vibratable member(s) of the resonating sensor unit(s).

Furthermore, in accordance with an embodiment of the present invention, the one or more resonating sensor units are embedded in the at least one body of gel.

Furthermore, in accordance with an embodiment of the present invention, the at least one body of gel completely covers all the vibratable members included in the resonating sensor unit(s).

Furthermore, in accordance with an embodiment of the present invention, the gel is selected from a synthetic gel, a natural gel, a hydrogel, a lipogel, a hydrophobic gel, a hydrophilic gel, a biocompatible gel, a hemocompatible gel, a polymer based gel, a cross-linked polymer based gel and combinations thereof.

Furthermore, in accordance with an embodiment of the present invention, the protected sensor further includes a housing.

Furthermore, in accordance with an embodiment of the present invention, the gel at least partially fills the housing.

Furthermore, in accordance with an embodiment of the present invention, the at least one body of gel comprises at least one thin layer of gel attached to the at least one vibratable member of the resonating sensor unit(s).

Furthermore, in accordance with an embodiment of the present invention, the resonating sensor unit(s) are disposed within at least one open chamber.

Furthermore, in accordance with an embodiment of the present invention, the at least one chamber is at least one chamber formed within a sensor anchoring device, or is at least one chamber comprising part of a sensor anchoring device.

Furthermore, in accordance with an embodiment of the present invention, the sensor anchoring device is selected from a sensor anchor, a sensor positioner, an implantable graft, a sensor fixating device, an implant, an implantable device, an implantable graft, a part of an implantable device, a pacemaker, a part of a pacemaker, a defibrillator, a part of a defibrillator, an implantable electrode, an insertable electrode, an endoscopic device, a part of an endoscopic device, an autonomous endoscopic device, a part of an autonomous endoscopic device, a tethered endoscopic device, a part of a tethered endoscopic device, an implantable catheter, an insertable catheter, a stent, a part of a stent, a guide-wire, a part of a guide-wire, an implantable therapeutic substance releasing device, and an insertable therapeutic substance releasing device.

Furthermore, in accordance with an embodiment of the present invention, the resonating sensor unit(s) may be selected from a passive sensor unit, an active sensor unit, a passive resonating sensor unit, an active resonating sensor unit, a pressure sensor, a passive ultrasonic pressure sensor, an active ultrasonic pressure sensor, and a sensor for sensing the concentration of a chemical species in a measurement environment.

Furthermore, in accordance with an embodiment of the present invention, at least one resonating sensor unit of the one or more resonating sensor units includes a substrate having one or more recesses formed therein, and a second layer sealingly attached to the substrate to form one or more sealed sensor unit chambers within the at least one resonating sensor unit.

Furthermore, in accordance with an embodiment of the present invention, the at least one vibratable member of the at least one resonating sensor unit is selected from at least one vibratable member comprising a portion of said substrate, and at least one vibratable member comprising a portion of the second layer overlying the recess(es).

Furthermore, in accordance with an embodiment of the present invention, each sealed sensor unit chamber of the one or more sealed sensor unit chambers has a pressure level therewithin.

Furthermore, in accordance with an embodiment of the present invention, the pressure level is a zero pressure level or a non-zero pressure level.

Furthermore, in accordance with an embodiment of the present invention, the protected sensor includes a first resonating sensor unit having one or more sealed sensor unit chambers and at least a second resonating sensor unit having one or more sealed sensor unit chambers, and the pressure level within at least one sealed sensor unit chamber of the first resonating sensor unit is different than the pressure level within at least one sealed sensor unit chamber of the at least second resonating sensor unit.

Furthermore, in accordance with an embodiment of the present invention, the one or more resonating sensor units are passive ultrasonic pressure sensor unit(s) having a single vibratable membrane, or passive ultrasonic pressure sensor unit(s) having multiple vibratable membranes.

Furthermore, in accordance with an embodiment of the present invention, the protected sensor is an implantable protected sensor.

Furthermore, in accordance with an embodiment of the present invention, one or more of the components of the implantable protected sensor includes one or more materials selected from biocompatible materials and hemocompatible materials.

Furthermore, in accordance with an embodiment of the present invention, the protected sensor is configured for implantation within a measurement environment. The measurement environment may be an eye, a urether, a cardiac chamber, a cardiovascular system, a part of a cardiovascular system, an annurismal sac after endovascular repair, a spine, an intervertebral disc, a spinal cord, a spinal column, an intracranial compartment, an intraluminal space of a blood vessel, an artery, a vein, an aorta, a pulmonary blood vessel, a carotid blood vessel, a brain blood vessel, and a coronary artery, a femoral artery, an iliac artery, a hepatic artery, a renal artery and a vena cava.

Furthermore, in accordance with an embodiment of the present invention, at least part of the surface of the protected sensor is a modified surface having modified surface properties.

Furthermore, in accordance with an embodiment of the present invention, the modified surface properties may be physical surface properties, chemical surface properties, electrochemical surface properties, biological surface properties, surface resistance to deposition of cells or tissues thereon, rheological surface properties, and any combinations thereof.

Furthermore, in accordance with an embodiment of the present invention, the modified surface is a chemically treated surface.

Furthermore, in accordance with an embodiment of the present invention, the modified surface is a surface of the gel.

Furthermore, in accordance with an embodiment of the present invention, the protected sensor also includes at least one non-resonating sensor unit.

Furthermore, in accordance with an embodiment of the present invention, the gel may include at least one releasable substance.

Furthermore, in accordance with an embodiment of the present invention, the releasable substance(s) may be selected from the group consisting of a protein, a peptide, a drug, a therapeutic agent, a polysaccharide, a lipid, a glycolipid, a lipoprotein, a glycoprotein, a proteoglycans, an extracellular matrix component, a nucleic acid, a polynucleotide, RNA, DNA, an anti-sense nucleic acid sequence, a receptor, an enzyme, an antibody, an antigen, an enzyme inhibitor, a cell proliferation inhibitor, a growth regulating factor, a growth inhibiting factor, a growth promoting factor, an anti-coagulant agent, an anti-clotting agent, a tumor inhibiting drug, a tumor inhibiting factor, a tumor suppressing agent, an anti-cancer drug, and any combinations thereof.

Furthermore, in accordance with an embodiment of the present invention, the gel comprises a substantially non-compressible gel.

Furthermore, in accordance with an embodiment of the present invention, the gel comprises a gel having a composition capable of retarding or reducing the diffusion of one or more substances into the gel.

Furthermore, in accordance with an embodiment of the present invention, the gel comprises a gel having a composition capable of retarding or reducing the deposition of one or more substances onto the vibratable member(s) of the resonating sensor unit(s).

There is also provided, in accordance with an embodiment of the present invention, a protected sensor including at least one resonating sensor unit. Each sensor unit of the at least one resonating sensor unit has at least one vibratable member having a resonance frequency that varies as a function of a physical variable in a measurement environment. At least one vibratable member of the resonating sensor unit(s) is protected by a gel attached thereto.

There is also provided, in accordance with an embodiment of the present invention, a method for constructing a protected a resonating sensor. The method includes the step of providing one or more resonating sensor units, each sensor unit of the one or more resonating sensor units has at least one vibratable member having a resonance frequency that varies as a function of a physical variable in a measurement environment. The method also includes the step of attaching at least one body of gel to the resonating sensor unit(s).

Furthermore, in accordance with an embodiment of the present invention, the step of attaching comprises covering all the vibratable members of the resonating sensor unit(s) with the gel.

Furthermore, in accordance with an embodiment of the present invention, the step of attaching comprises applying a liquefied gel to cover at least the vibratable member(s) of the resonating sensor unit(s) with the liquefied gel, and allowing the liquefied gel to solidify.

Furthermore, in accordance with an embodiment of the present invention, the liquefied gel is obtained by heating a liquefiable gel.

Furthermore, in accordance with an embodiment of the present invention, the step of attaching comprises applying a liquid comprising at least one gel precursor to cover at least the vibratable members of the resonating sensor unit(s) with the liquid, and allowing said the gel to form from the liquid.

Furthermore, in accordance with an embodiment of the present invention, the gel precursor(s) comprise at least one monomer capable of being polymerized to form the gel.

Furthermore, in accordance with an embodiment of the present invention, the step of attaching comprises embedding the resonating sensor unit(s) within at least one body of gel.

Furthermore, in accordance with an embodiment of the present invention, the step of attaching comprises completely embedding or partially embedding the resonating sensor unit(s) in at least one body of gel attached to a surface.

Furthermore, in accordance with an embodiment of the present invention, the surface is selected from, a surface of a sensor housing, a surface of a sensor anchoring device, a surface of an implantable graft, a surface of an implantable device, a surface of an implant, a surface of an insertable device, and a surface of an enclosure surrounding a measurement environment.

Furthermore, in accordance with an embodiment of the present invention, the acoustic impedance of the gel is close to or equal to the acoustic impedance of a medium contained in a measurement environment in which the protected sensor is disposed.

Furthermore, in accordance with an embodiment of the present invention, the protected sensor is an implantable protected sensor configured for implantation within an organism and the acoustic impedance of the gel is close to or equal to the acoustic impedance of at least one tissue or bodily fluid of the organism.

Furthermore, in accordance with an embodiment of the present invention, the step of attaching comprises disposing the resonating sensor unit(s) in a housing, at least partially filling the housing with a liquid comprising at least one gel precursor to cover at least a vibratable member of the resonating sensor unit(s) with the liquid, and allowing the gel to form from the liquid.

Furthermore, in accordance with an embodiment of the present invention, the protected resonating sensor also includes at least one non-resonating sensor unit, and the step of attaching comprises attaching the non-resonating sensor unit(s) to the at least one body of gel.

Furthermore, in accordance with an embodiment of the present invention, the method further includes the step of treating at least part of the surface of the protected sensor for modifying the surface properties of thereof.

Furthermore, in accordance with an embodiment of the present invention, the step of treating is performed on the gel to change the surface properties thereof.

Furthermore, in accordance with an embodiment of the present invention, the surface properties modified by the step of treating are selected from physical surface properties, chemical surface properties, electrochemical surface properties, biological surface properties, surface resistance to deposition of cells or tissues thereon, rheological surface properties, and any combinations thereof.

Furthermore, in accordance with an embodiment of the present invention, the step of treating comprises chemically treating at least part of the surface of the protected sensor for modifying the surface properties thereof.

Furthermore, in accordance with an embodiment of the present invention, the method further includes the step of incorporating at least one releasable substance in the gel.

Furthermore, in accordance with an embodiment of the present invention, the at least one releasable substance is selected from the group consisting of a protein, a peptide, a drug, a therapeutic agent, a polysaccharide, a lipid, a glycolipid, a lipoprotein, a glycoprotein, a proteoglycans, an extracellular matrix component, a nucleic acid, a polynucleotide, RNA, DNA, an anti-sense nucleic acid sequence, a receptor, an enzyme, an antibody, an antigen, an enzyme inhibitor, a cell proliferation inhibitor, a growth regulating factor, a growth inhibiting factor, a growth promoting factor, an anti-coagulant agent, an anti-clotting agent, a tumor inhibiting drug, a tumor inhibiting factor, a tumor suppressing agent, an anti-cancer drug, and any combinations thereof.

Furthermore, in accordance with an embodiment of the present invention, the step of incorporating comprises adding the at least one releasable substance to the gel prior to disposing the gel in the protected sensor.

Furthermore, in accordance with an embodiment of the present invention, the step of adding is selected from, adding the at least one releasable substance to a liquid gel precursor, and adding the at least one releasable substance to a liquefied gel.

Furthermore, in accordance with an embodiment of the present invention, the step of incorporating comprises introducing the at least one releasable substance to the gel after disposing the gel in said protected sensor.

Furthermore, in accordance with an embodiment of the present invention, the step of introducing comprises diffusing the at least one releasable substance into the gel.

Furthermore, in accordance with an embodiment of the present invention, the diffusing comprises incubating the protected sensor in a solution comprising the at least one releasable substance.

There is also provided, in accordance with an embodiment of the present invention, a method for constructing a protected resonating sensor. The method includes the steps of: providing one or more resonating sensor units, each sensor unit of the resonating sensor unit(s) has at least one vibratable member having a resonance frequency that varies as a function of a physical variable in a measurement environment, and covering the at least one vibratable member of the one or more resonating sensor units with a gel.

There is also provided, in accordance with an embodiment of the present invention, a method for constructing a protected resonating sensor. The method includes the steps of: providing one or more resonating sensor units, each sensor unit of the resonating sensor unit(s) has at least one vibratable member having a resonance frequency that varies as a function of a physical variable in a measurement environment, and providing a gel in contact with said at least one vibratable member of said one or more resonating sensor units.

There is also provided, in accordance with an embodiment of the present invention,.a method for protecting a resonating sensor unit having one or more vibratable members. The method includes the step of covering at least the one or more vibratable members of the sensor unit with a gel.

There is also provided, in accordance with an embodiment of the present invention, a method for protecting a resonating sensor unit having one or more vibratable members. The method includes the step of covering at least one vibratable member of the sensor unit with a gel.

DETAILED DESCRIPTION OF THE INVENTION

The present invention discloses novel resonating sensors in which the vibratable part of the sensor is protected from deposition of undesirable materials or cells or tissues or other undesirable deposits, and methods for constructing such protected sensors.

In accordance with one possible embodiment of the present invention, the vibratable resonating part or parts of the resonating sensor are protected by using a protective compliant membrane coupled to the vibratable part(s) of the sensor(s) by a non-compressible medium. For the purposes of the present application, the term non-compressible medium defines any suitable substantially non-compressible liquid or any suitable substantially non-compressible gel. The physical variable to be measured (such as, but not limited to, pressure and temperature) is transferred to the vibratable part(s) of the resonating sensor with minimal attenuation while the compliant membrane prevents the accumulation or deposition of extraneous substances on the vibratable part of the sensor.

In accordance with another possible embodiment of the present invention, the vibratable resonating part or parts of the resonating sensor unit(s) may be protected by covering or coating the vibratable part(s) of the sensor(s) with a body or a layer of gel. Since such protected sensors do not have a compliant member, and at least part of the gel is in direct contact with the medium disposed in the measurement environment, this type of sensors may be referred to as "open protected sensors". As disclosed in detail hereinafter, the body of gel or the layer of gel for protecting the vibratable (resonating) part(s) of the sensor may be attached to the resonating part(s) of the sensor(s) or sensor unit(s) using any method known in the art for gel forming, including, but not limited to casting, coating, dipping, gel polymerization and/or cross-linking, or the like. Alternatively the entire sensor (including one or more resonating sensor units) may be embedded or partially embedded in a body of gel. Generally, any suitable method for forming a gel may be used as is known in the art. The physical variable to be measured (such as, but not limited to, pressure and temperature) is transferred to the vibratable part(s) of the resonating sensor with minimal attenuation while the body of gel or the layer of gel prevents the accumulation or deposition of extraneous substances on the vibratable part of the sensor. Preferably (but not obligatorily), in open protected resonating pressure sensors, the gel may be a substantially non-compressible gel. Other open resonating sensors (such as, but not limited to, protected resonating temperature sensors, protected resonating sensors for determining the concentration of a chemical species, and the like) may use compressible gels.

The open protected sensors of the present invention may include passive and/or active resonating sensor unit(s) that are interrogated by sonic or ultrasonic energy. The open protected sensors of the present invention may also include any other type of passive or active sensor unit or units (which may or may not be resonating sensor unit or units) known in the art, provided that their operation is not undesirably affected by the gel used in the protected sensor.

It is noted that, while most of the particular examples described in detail hereinafter and illustrated in the drawing figures are adapted for passive ultrasonic resonating sensors, the method of protection of a resonating sensor may be similarly applied to any type of resonating sensors including resonating parts which may be detrimentally affected by the deposition or accumulation of extraneous substance(s) or material(s) or tissues or cells on the surface of the resonating part of the sensor. Thus, the method of protection of resonating sensors of the present invention is a general method and may be applied to many different types of resonating sensors, such as, but not limited to, active or passive acoustic resonating sensors, active or passive ultrasonic sensors, active or passive optically interrogated sensors, capacitive resonating sensors, active resonating sensors having an internal energy source or coupled to an external energy source by wire or wirelessly, or the like, as long as the sensors is interrogated using sonic energy.

Figure 8:
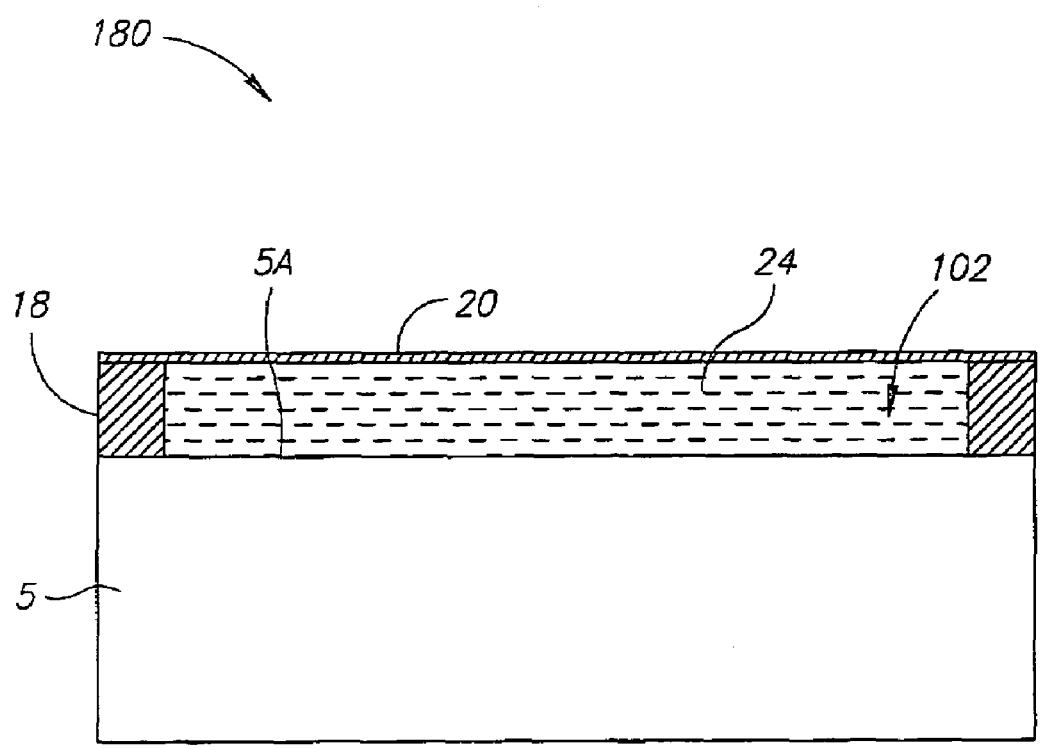
FIG. 8 is a schematic part cross-sectional diagram illustrating a general form of a protected resonating sensor in accordance with an embodiment of the present invention.

Thus, as will be appreciated by those skilled in the art, the methods of protecting resonating sensors disclosed herein may be applied to any suitable type of resonating sensor known in the art which has one or more resonators or resonating parts exposed to a measurement environment or medium (see FIG. 8 for a schematic illustration of a protected resonating sensor).

Reference is now made to FIG. 1 which is a schematic cross-sectional view of a protected passive ultrasonic pressure sensor having multiple vibratable membranes, in accordance with an embodiment of the present invention.

The protected sensor 10 may include a sensor unit 82. The sensor unit 82 may include a first recessed substrate layer 12 and a second layer 14 sealingly attached to the first recessed layer 12. The first recessed layer 12 has a plurality of recesses 16 formed therein. While only three recesses 16 are shown in the cross-sectional view of FIG. 1, the protected sensor 10 may be designed to include any practical number of recesses (such as for example, one recess, two recesses, three recesses or more than three recesses 16). For example, the protected sensor 10 may include nine recesses 16 arranged three rows having three recesses per row (not shown in FIG. 1).

The first recessed substrate layer 12 and the second layer 14 may be made from any suitable material such as, but not limited to, a metal, silicon, Pyrex®, boron nitride, glass, or the like. Preferably (but not obligatorily), the first substrate layer 12 is made from a material such as silicon, Pyrex® or another suitable material that is amenable to machining using standard lithography methods known in the art (such as, for example, the forming of the recesses 16 in the first substrate layer 12 using conventional masking, photoresist application and etching methods, and the like). However, other machining or micromachining, or processing methods known in the art may also be used with appropriate selection of other desired materials for constructing the sensor units of the present invention.

The second layer 14 is sealingly attached or glued or affixed to the first layer 12 to form a plurality of sealed sensor unit chambers 17. As disclosed hereinabove, while the cross-sectional view of FIG. 1 shows only three sealed sensor unit chambers 17, there may or may not be more than three sealed sensor unit chambers in the protected sensor 10. For example, the protected sensor 10 may include nine sealed sensor unit chambers 17 arranged three rows each row having three chambers per row, in an arrangement similar to the multi-membrane sensor disclosed in detail in FIGS. 2 and 3 of U.S. patent application to Girmonsky et al., Ser. No. 10/828,218. The parts labeled 14A, 14B and 14C of the second layer 14 lying above the recesses 16 represent the vibratable membranes 14A, 14B and 14C of the protected sensor 10.

The protected sensor 10 may also include a spacer 18 attached to the sensor unit 82. The spacer 18 may be made from a rigid material such as, but not limited to, a metal, silicon, boron nitride, glass, or a polymer based material such as SU8® epoxy based photoresist (commercially available from MicroChem Corp., Mass., U.S.A), or the like.

While the spacer 18 is shown as a separate component sealingly attached or glued to the second layer 14 of the sensor unit 82, in other possible embodiments the spacer 18 may be formed as a part of the second layer 12, or as a part of the first recessed layer 12. The protected sensor 10 also includes a compliant member 20 sealingly attached to the spacer 18 to form a sealed chamber 22 (by using a suitable glue or any other suitable method known in the art for sealingly attaching the compliant member 20 to the spacer 18). The compliant member 20 may be made from a thin membrane that has a high compliance. For example, in accordance with one implemented embodiment of the present invention, the compliant member 20 may be a Kapton® membrane having a thickness of about nine micrometers.

It is noted that when selecting the material from which the compliant member 20 is made, care should be taken to ensure that the acoustic impedance of the selected material (for propagation of ultrasound) is matched to the acoustic impedance of the medium 24, and to the acoustic impedance of the material or medium in which the sensor is disposed. This matching may prevent excessive reflection of ultrasound at the interface between the medium in the measurement environment and the compliant member 20 and at the interface between the compliant member 20 and the medium 24. While it may not always be possible to obtain the best impedance match for each and every application due to practical constraints in the choice of the material(s) forming the non-compressible medium 24 and the compliant member 20 and compromises may have to be made, such impedance matching should be carefully considered in the design and implementation of the protected sensors of the present invention in order to improve sensor performance.

In accordance with additional embodiments of the present invention, the compliant member 20 may also be made from suitable Polyurethane rubbers, such as, but not limited to 6400 Polyurethane rubber or 6410 Polyurethane rubber, commercially available from Ren Plastics, USA. The compliant member 20 may also be made from RTV60 commercially available from GE Corporation, USA. In implantable sensors, when RTV 60 is used, the RTV 60 may preferably be mixed with 1% (by weight) of tungsten powder (of approximately 1 micron mean particle size) to adjust the acoustic impedance of the compliant member 20 to a value of approximately 1.5-1.54 Mrayls (Mrayl=$10^6$ rayl), which is close to the acoustic impedance of some tissues. However, this acoustic impedance value range is not limiting and other different values of acoustic impedance of the compliant member 20 may also be acceptable, depending, inter alia on the specific application, and the detection system's sensitivity. In accordance with other embodiments of the invention, for sensors configured to be implanted in mammals or humans, the compliant member 20 may be preferably made of Echothane CPC41 or Echothane CPC-29, both commercially available from Emerson Cummings, 604 W 182nd St., Gardena, Calif., USA. These materials have acoustic impedance values (in the ultrasound range) which exhibit an acceptable match to the acoustic impedance of water (in a sensor in which water is used as the medium 24) and tissue.

It is, however, noted that the compliant member 20 may be made from or may include any other suitable highly compliant materials known in the art, and the thickness and/or dimensions and/or composition of the compliant member 20 may be varied according to, inter alia, the sensor's specific design, the desired sensor performance, the medium in which the sensor is disposed during measurement, the pressure and temperature ranges within which the sensor needs to be operated, and other manufacturing and construction parameters and considerations.

The sealed chamber 22 may be filled with a non-compressible medium 24. The non-compressible medium 24 may be a substantially non-compressible liquid, such as but not limited to water or may be any other suitable substantially non-compressible liquid known in the art, such as, but not limited to, suitable silicon oil formulations, or the like. The non-compressible medium 24 may also be a suitable substantially non-compressible gel, such as, but not limited to, gelatin, agarose, a naturally occurring gel, a polymer based synthetic gel, a cross-linked polymer based gel, a hydrogel, or any other suitable type of gel known in the art. In certain applications, the protected sensor may need to be sterilized, such as, for example, in sensors that need to be implanted in a living body, or in sensors that are to be placed in sterile environments, such as in bioreactors or the like. In such applications, the medium 24 may be (but is not limited to) low vapor pressure liquids such as the Dow Corning 710(R) Silicon Fluid, commercially available from Dow Corning Inc., U.S.A. In other applications, the medium 24 may be a liquid such as a mixture of Fluorinert FC40 fluid and Fluorinert FC 70 fluid (about 60:40 by volume), both fluids are commercially available from 3M corporation, USA, or other suitable mixtures having different ratios of these fluids, or similar suitable Fluorinert fluids or mixtures thereof.

The use of low viscosity low vapor pressure liquids may be advantageous in such applications requiring sensor sterilization and in other applications types, because if one uses heat to sterilize the protected sensor, the use of low vapor pressure liquids as the medium 24 avoids the developing of a high pressure within the sealed chamber 22 and subsequent rupture of the compliant member 20. For similar reasons, the use of low vapor-pressure liquids or gels may be advantageous in applications in which the sensor is placed in a high temperature environment, to avoid rupture of the compliant member 20.

In applications in which the sensor is sterilized using gas phase chemical sterilization requiring exposing the sensor to a sterilizing gas under low pressure conditions it may also be preferred to use a low-vapor pressure medium within the sealed chamber 22 to prevent rupture of the compliant member 20.

The compliant member 20 may be designed and constructed such that it's resonance frequency is sufficiently low compared to the frequency range within which the vibratable membranes (such as, for example, the vibratable membranes 14A, 14B and 14C of the protected sensor 10) vibrate within the working pressure range of the protected sensor 10, to avoid the affecting of the measured signal by frequencies associated with vibrations of the compliant member 20.

Generally, the composition of the compliant member 20 should be adapted to the application by selecting a material that is suitably chemically resistant to the medium (gas or liquid) within the measurement environment to avoid excessive degradation or corrosion of the compliant member 20. In sensors that are designed to be implanted within a body in-vivo, the compliant member 20 is preferably made from (or covered with or coated with), a biocompatible material. It is noted that while Echothane—CPC-41 or Echothane—CPC-29 disclosed hereinabove may be suitable sufficiently compliant and biocompatible materials for implementing the compliant member 20, other different materials may also be used to construct the compliant member 20, such as, but not limited to, polymer based materials, biocompatible polymers, polyurethane, ethyl vinyl acetate based polymers, a Parylene®C based polymer or other suitable compliant materials.

Additionally, care should be taken in selecting the medium 24 and the material from which the compliant member 20 is made such that the reflection of the interrogating ultrasound beam from the interface between the medium in the measurement environment (not shown) and the compliant member 20 or from the interface between the compliant member 20 and the medium 24 is relatively small to avoid excessive reflection of the interrogating beam from these interfaces and a concomitant reduction in the portion of the energy of the interrogating ultrasound beam which reaches the vibratable membranes of the sensor. This may be practically achieved by selecting the material of the compliant member 20 and the medium 24 such that the acoustic impedance of the compliant membrane 20 and in the non-compressible medium 24 are reasonably close to the acoustic impedance of the medium in which the protected sensor 10 is disposed during measurement.

The sealed sensor unit chambers 17 may include a gas or a mixture of gases therewithin. When the sealed sensor unit chambers 17 are formed, the pressure within the sealed sensor unit chambers 17 is set to a value of P1. After construction of the protected sensor 10, when the protected sensor 10 is disposed in a measurement environment or medium, the pressure value in the measurement environment or medium in which the protected sensor 10 is disposed is represented by P2 (FIG. 1).

Since the medium 24 is substantially non-compressible, and the compliant member 20 has a high compliance, the pressure P2 acting on the compliant member 20 is transmitted by the compliant member 20 to the vibratable membranes 14A, 14B and 14C through the medium 24. Therefore, within a certain pressure value range, the surfaces of the vibratable membranes 14A, 14B and 14C contacting the medium 24 are subjected to practically the same pressure value P2. Thus, within the practical working pressure range of the protected sensor 10 all the vibratable membranes (including any vibratable membranes not shown in the cross-sectional view of FIG. 1) of the sensor 10 will effectively experience on their surfaces which are in contact the medium 24 the external pressure P2 acting on the protected sensor 10.

When the pressure P1 inside the sealed sensor unit chambers 17 equals the external pressure P2 in the measurement environment (P1=P2), the vibratable membranes of the sensor unit 82, (such as, for example, the vibratable 14A, 14B, and 14C) are substantially minimally stressed.

In situations in which P1≠P2, the vibratable membranes of the sensor unit 82 (such as, for example, the vibratable 14A, 14B, and 14C) are pushed by the pressure difference and become curved and therefore become stressed. The absolute value of the difference between the external pressure P2 in the measurement medium and the pressure P1 within the sealed sensor unit chambers 17 of the sensor unit 82 is $\Delta P=|(P2-P1)|$. The stress in the vibratable membranes depends on $\Delta P$.

The resonance frequency of the vibratable membranes of the sensor unit 82 depends on the stress in the vibratable membranes of the sensor unit 82. The resonance frequency is lowest when the vibratable membranes are minimally stressed. As the stress in the vibratable membranes increases, the resonance frequency of the vibratable membranes increases accordingly. Thus, since the resonance frequency $f_R$ of the vibratable membranes is a function of $\Delta P$, when one determines the resonance frequency of the vibratable membranes of the sensor unit 82, it is possible to determine $\Delta P$ (the absolute value of the pressure difference) from $f_R$. By properly selecting the internal pressure P1, it is possible to determine the value of P2 from the measured resonance frequency of a calibrated passive ultrasonic sensor (such as, but not limited to the protected sensor 10 shown in FIG. 1). For example, in a simple case, if we set P1=0 (by creating vacuum in the sealed sensor unit chambers 17 of the sensor unit 82 during manufacturing of the sensor) then $\Delta P=P2$, enabling direct determination of the pressure P2.

Thus, the protected sensor 10 may be pre-calibrated prior to use, enabling the use of a calibration curve or a look-up table (LUT) for directly obtaining the pressure P2 from the measured resonance frequency $f_R$ of the vibratable membranes (or vibratable parts, depending on the sensor type) of the passive sensor. It is, however, noted that if the sealed sensor unit chambers 17 of the sensor 10 have a non-zero internal pressure level (which is the case when the sealed sensor unit chambers 17 include a gas or gases therein and therefore have a substantial non-zero internal pressure level), the pressure may have to be corrected to take into account the effects of temperature on the gas (or gases) enclosed within the sealed sensor unit chambers 17.

Methods for measuring the resonance frequency of passive ultrasonic sensors are known in the art, are not the subject matter of the present invention, and are therefore not disclosed in detail hereinafter. Briefly, a beam of exciting ultrasound may be directed toward the sensor, the resonance frequency of the sensor may be determined from the ultrasonic signal returning from the sensor (or, alternatively, by determining the amount of energy absorbed by the sensor from the exciting beam). The interrogating ultrasonic beam may be continuous, pulsed or chirped. Such methods are disclosed, inter alia, in U.S. Pat. Nos. 5,619,997, 5,989,190 and 6,083,165 to Kaplan.

Another method for determining the resonance frequency of passive ultrasonic sensors by using the Doppler effect is disclosed in co-pending U.S. patent application Ser. No. 10/828,218 to Girmonsky et al.

It is noted that the schematic cross-sectional illustration of FIG. 1 represents a situation in which P1>P2. Because of this pressure difference, the vibratable membranes 14A, 14B and 14C are shown as having a curved shape which is convex in the direction of the compliant member 20 (it is noted that the degree of curvature of the vibratable membranes 14A, 14B and 14C is exaggerated in all the drawing figures, for clarity of illustration). In a situation in which P1=P2 (not shown), the vibratable membranes of the sensor unit 82 may or may not be flat (planar), depending, inter alia, on the sensor's structure and implementation. For example, if the sensor is coated by a layer of coating material (not shown), the vibratable membranes 14A, 14B and 14C may be curved even in cases in which P1=P2. Furthermore, in sensors in which the vibratable membranes 14A, 14B and 14C are pre-stressed at manufacturing time, the vibratable membranes 14A, 14B and 14C may be curved even in cases in which P1=P2. In a situation in which P1<P2 (not shown), the vibratable membranes of the sensor unit 82 may be curved such that the side of the vibratable membrane facing the cavity of the sealed sensor unit chamber 17 is convex.

The operability of the protected sensors of the invention was experimentally tested as follows. The experiment was performed using the multi-membrane passive ultrasonic pressure sensor 20 illustrated in FIGS. 2 and 3 of co-pending U.S. patent application Ser. No. 10/828,218 to Girmonsky et al.

The nine sensor sealed chambers 29A, 29B, 29C, 29D, 29E, 29F, 29G, 29H and 29I of the sensor (of co-pending U.S. patent application Ser. No. 10/828,218 to Girmonsky et al.)

were filled with air. The non-protected sensor was placed in a controlled pressure chamber, covered with water and interrogated at various different pressure levels by an ultrasonic beam having a carrier frequency at 750 KHz and eleven sensor exciting frequencies of 72 KHz, 74 KHz, 76 KHz, 78 KHz, 80 KHz, 82 KHz, 84 KHz, 86 KHz, 88 KHz, 90 KHz and 92 KHz using the Doppler method disclosed by Girmonsky et al. in the above referenced co-pending U.S. patent application Ser. No. 10/828,218, to determine the resonance frequency of the sensor at each known pressure level in the pressure chamber.

A small stainless steel ring-like washer was then placed on a holder in the controlled pressure chamber such that the sensor was at the approximate center of the shallow opening of the washer (the height of the washer was greater than the height of the sensor. A thin compliant film of polyethylene having a thickness of approximately 9 microns was held in a suitable frame and lowered carefully onto the washer until it was firmly attached to the upper surface of the washer. A water-filled chamber was thus formed by the washer and the overlying compliant polyethylene film such that the vibratable membranes of the sensor were opposed to the compliant polyethylene film, and the space formed by the washer and the attached polyethylene film was completely filled with water to form a protected sensor.

The same series of resonance frequency versus pressure measurements as performed on the non-protected sensor were performed again by repeating the measurements of the resonance frequencies for the same experimental pressure levels with the protected sensor. When the dependence of the sensor's resonance frequency on the pressure level was compared for the first and second sets of measurements (performed with the non-protected sensor and with the protected sensor, respectively), there was no substantial difference between the data set for the non-protected sensor and for protected sensor. This experiment indicates that the tested sensor may be protected by a compliant member without substantially affecting the dependence of the resonance frequency of the sensor's vibratable membranes on the external pressure.

It is noted that various structural and design modifications may be made in implementing the protective sensors of the present invention. For example, while in the protected sensor 10 of FIG. 1, the spacer 18 and the compliant member 20 are attached to the sensor unit 82, other different configurations are possible.

Figure 2:
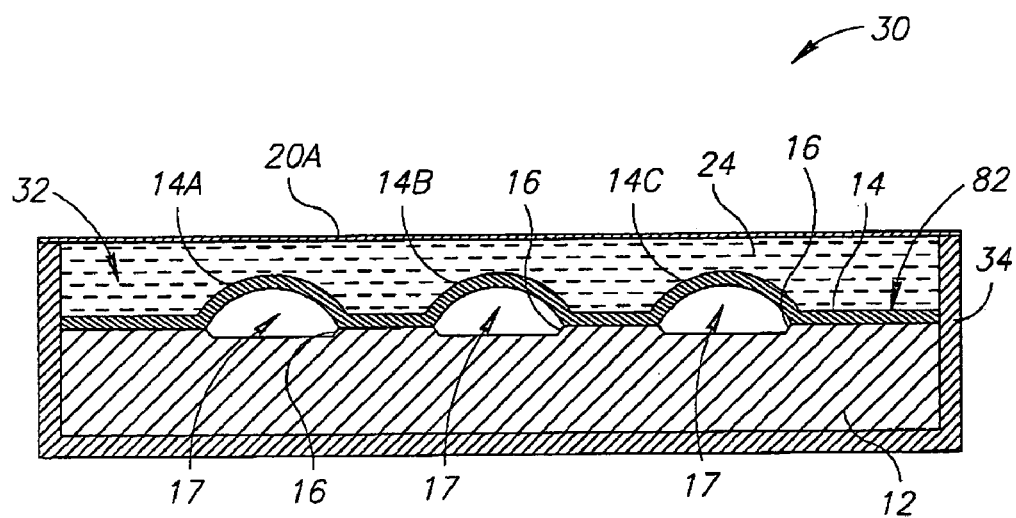
FIG. 2 is a schematic cross-sectional view illustrating a protected passive ultrasonic pressure sensor enclosed in a housing, in accordance with an additional embodiment of the present invention.

Reference is now made to FIG. 2 Which is a schematic cross-sectional view illustrating a protected passive ultrasonic sensor enclosed in a housing, in accordance with an additional embodiment of the present invention.

In the protected sensor 30, the first recessed substrate layer 12, the second layer 14, the plurality of recesses 16, the sealed sensor unit chambers 17, and the vibratable membranes 14A, 14B and 14C are as disclosed in detail hereinabove for the sensor 10. The first substrate layer 12 and the second substrate layer 14 are attached together to form the sensor unit 82 which is disposed or attached within a rigid housing 34. The housing 34 may include a rigid material such as, but not limited to, a metal, a metal alloy, titanium, platinum, stainless steel, a shape memory alloy such as but not limited to NITINOL®, silicon, glass, quartz, a ceramic material, a composite material, a metallic or non-metallic nitride, boron nitride, a carbide, a metal oxide, a non-metallic oxide, a polymer based material, and combinations thereof. Such polymer based materials may include, but are not limited to, Delrin® (commercially available from Dupont, USA), or the like.

For implantable sensors, the housing 34 may preferably be made from a biocompatible material such as titanium, platinum, or the like (including any biocompatible substances disclosed herein), or alternatively may be covered by a layer of biocompatible material (not shown) such as, but not limited to, Parylene®, or the like. A compliant member 20A is sealingly attached to the housing 34 to form a sealed chamber 32. The compliant member 20A is as described in detail hereinabove for the compliant member 20 of the sensor 10.

The sealed chamber 32 is completely filled with the substantially non-compressible medium 24, as disclosed hereinabove for the chamber 22 of the protected sensor 10. The combination of the housing 34, the compliant member 20A and the medium 24 protect the vibratable members (including, but not limited to, the vibratable members 14A, 14B and 14C illustrated in FIG. 2) of the protected sensor 30 from deposition of extraneous materials or tissues or cells, as disclosed hereinabove, without significantly attenuating the pressure transmitted to the vibratable membranes 14A, 14B and 14C of the protected sensor 30.

It is noted that, while the first recessed substrate layer 12 and the second layer 14 of the protected sensor 30 tightly fit into the housing 34 (and may also possibly be attached thereto by a suitable glue or by any other suitable attaching method known in the art), other configurations of a sensor attached within a sealed housing may also be implemented by those skilled in the art. For example, the external dimensions and/or shape of the sensor unit 82 (comprising the first recessed layer 12 and the second layer 14) may not precisely match the internal dimensions of the housing 34. Thus, in such an embodiment (not shown) the cross-sectional area of the housing of the sensor may be larger than the cross-sectional area of the unprotected sensor. Additionally, in accordance with another embodiment of the protected sensor of the present invention, more than one unprotected passive sensor may be disposed within a single protective housing.

Figure 3:
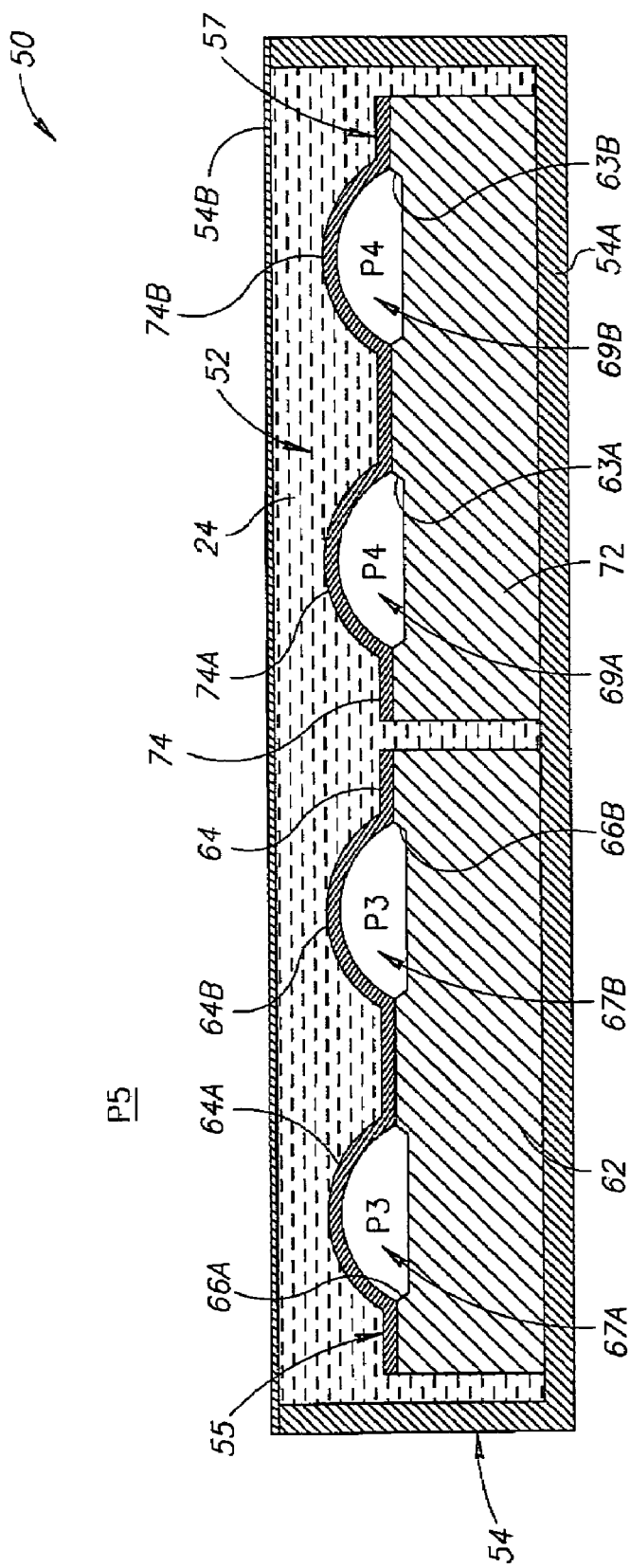
FIG. 3 is a schematic cross-sectional view illustrating a protected ultrasonic pressure sensor including two different passive ultrasonic sensor units disposed within a single protective housing, in accordance with an additional embodiment of the present invention.

Reference is now briefly made to FIG. 3 which is a schematic cross-sectional view of a protected ultrasonic sensor including two different passive ultrasonic sensor units disposed within a single protective housing, in accordance with an additional embodiment of the present invention.

The protected sensor 50 of FIG. 3 includes a protective housing 54. The housing 54 includes a housing part 54A, and a compliant member 54B. The housing part 54A may be made from any suitable material, such as, but not limited to a metal, glass, silicon, a plastic or polymer based material, or the like, as disclosed hereinabove for the housing 34 of FIG. 2. The compliant member 54B may be a highly compliant thin membrane made from Kapton®, Polyurethane, or from any other suitably compliant material, such as, but not limited to, a compliant polymer material, or the like, or any other suitable material known in the art.

The compliant member 54B may be sealingly attached to or glued to or suitably deposited on, or otherwise sealingly connected to the housing part 54A to form a sealed chamber 52. The protected sensor 50 further includes two passive ultrasonic sensor units 55 and 57. The passive ultrasonic sensor units 55 and 57 may be glued or attached or otherwise connected to the housing part 54A using any suitable attachment method or attaching materials known in the art.

The sensor unit 55 comprises a first recessed substrate layer 62 and a second layer 64. The parts 64A and 64B of the second layer 64 are vibratable membranes comprising the parts of the layer 64 which overlie recesses 66A and 66B formed within the first recessed substrate layer 62. While only two vibratable membrane parts 64A and 64B are shown in the cross-sectional view of FIG. 3, the sensor unit 55 may include one vibratable membrane or may include more than one vibratable membranes, as disclosed in detail hereinabove for the sensors 10 and 30 (of FIGS. 1 and 2, respectively). Thus, the sensor unit 55 may include any suitable number of vibratable membranes. The second layer 64 is suitably sealingly attached to the first recessed substrate layer 62 under suitable pressure conditions to form sealed sensor unit chambers (of which only sealed sensor unit chambers 67A and 67B are shown in the cross-sectional view of FIG. 3). The pressure within the sealed sensor unit chambers 67A and 67B is P3.

The sensor unit 57 comprises a first recessed substrate layer 72 and a second layer 74. The parts 74A and 74B of the second layer 74 are vibratable membranes comprising the parts of the layer 74 which overlie recesses 63A and 63B formed within the first recessed substrate layer 72. While only two vibratable membrane part 74A and 74B are shown in the cross-sectional view of FIG. 3, the sensor unit 57 may include one vibratable membrane or may include more than one vibratable membranes, as disclosed in detail hereinabove for the protected sensors 10 and 30 (of FIGS. 1 and 2, respectively). Thus, the sensor unit 57 may include any suitable number of vibratable membranes. The second layer 74 is suitably sealingly attached to the first recessed substrate layer 72 under suitable pressure conditions to form sealed sensor unit chambers (of which only sealed sensor unit chambers 69A and 69B are shown in the cross-sectional view of FIG. 3). The pressure within the sealed sensor unit chambers 69A and 69B is P4. The sensor units 55 and 57 may be manufactured such that P3=P4 or such that P3≠P4.

The sealed chamber 52 is completely filled with the substantially non-compressible medium 24 as disclosed hereinabove. The pressure P5 outside the protected sensor 50 is transmitted with minimal attenuation to the vibratable membranes of the sensor units 55 and 57 (such as, for example, the vibratable membranes 64A and 64b of the sensor unit 55 and to the vibratable membranes 74A and 74B of the sensor unit 57) through the compliant member 54B and the medium 24 as disclosed hereinabove.

The use of two (or, optionally, more than two) sensor units having different internal pressure values may be useful for providing temperature compensated pressure measurements, or for other purposes such as, but not limited to, providing an extended measurement range by including within the protected sensor two or more different pressure sensors each optimized for a particular pressure range. Additionally, one or more sensor units having similar internal sensor pressure values may be used within the same protected sensor to increase the protected sensor's signal strength, by increasing the total surface area of the vibratable membranes in the protected sensor.

It is noted that the protected sensor of the present invention may be implemented such that the protected sensor may be formed as part of a sensor anchoring device, or may be formed within a sensor anchoring device, or may be attached thereto. Such sensor anchoring device may be, but is not limited to, a sensor anchor (such as, but not limited to any of the devices disclosed in U.S. Pat. No. 6,331,163 to Kaplan), a sensor positioner, an implantable graft, any suitable part of an implantable device, a pacemaker, a defibrillator or a part thereof, an implantable electrode or a part thereof, an insertable electrode or a part thereof, an implantable catheter or a part thereof, an insertable catheter or a part thereof, a stent, a part of a stent, a guide-wire or a part thereof, an endoscopic device or a part thereof, an autonomous or a tethered endoscopic device or a part thereof, an implantable graft or other implant types, or any other suitable device which may be implanted in or inserted into in a body of any organism, animal or human patient.

It will be appreciated by those skilled in the art that the sensor anchoring devices to which the protected sensors of the present invention may be attached (or within which anchoring device such protected may be formed or included as a part thereof), are not limited to devices having the sole purpose of serving as a support or carrying platform for the protected sensor of the invention. Rather, the anchoring devices may have any other suitable structure and/or function that may or may not be related to the structure or function(s) of the protected sensor, and may also be used for other unrelated purposes besides functioning as a support for the protected sensor. For example, if a protected sensor is attached to or formed within or enclosed in an implanted electrode of a pacemaker, the electrode may function as a platform or member for carrying the protected sensor, while independently functioning as a stimulating and/or sensing electrode as is known in the art. Thus, the attachment of the protected sensors of the present invention to any device positionable in a measurement environment (or the inclusion thereof in such a device) may, but need not necessarily be associated with the functioning of the device.

Similarly, the sealed chamber of the protected sensors of the present invention may be formed within any such suitable sensor anchoring device or sensor supporting device or sensor fixating devices, or implantable grafts or other type of implant or implantable device. The sealed chamber of the protected sensors of the present invention may also be configured to comprise a part or as portion of any such suitable sensor anchoring device or sensor supporting device or sensor fixating devices, or implantable grafts or any other type of an implant or implantable device or stent, as a part of the sealed chamber.

Figure 4:
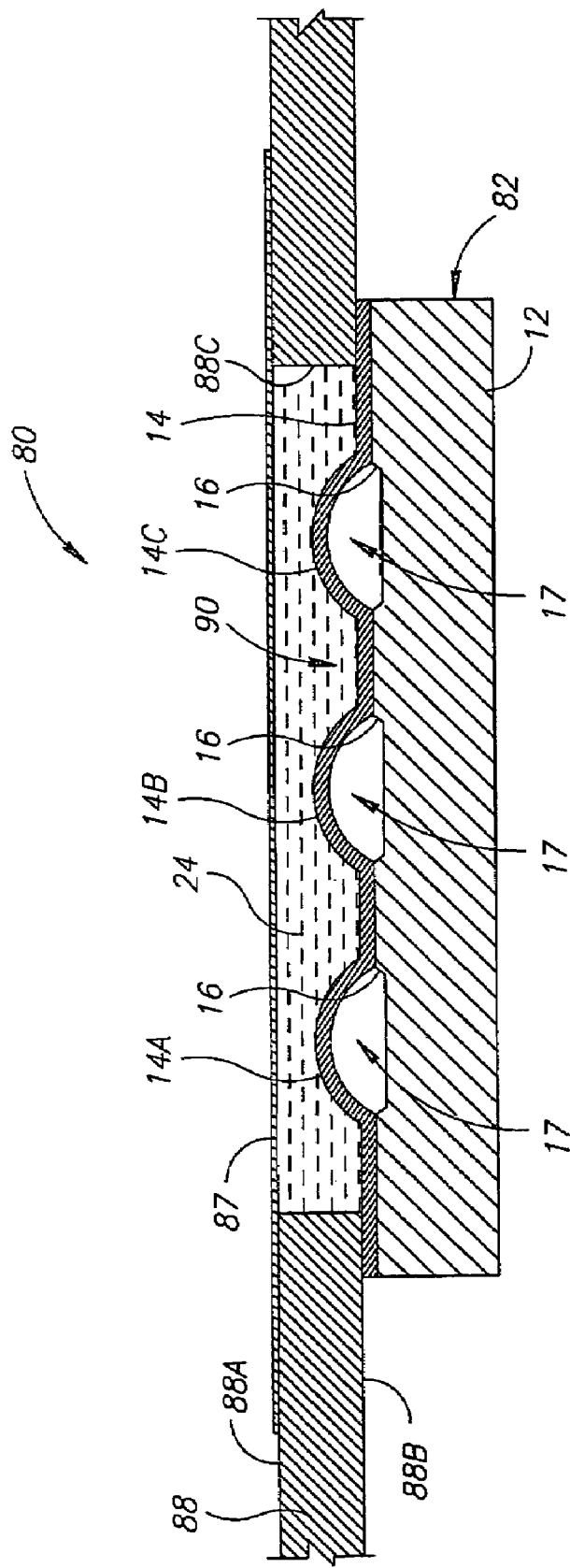
FIG. 4 is a schematic cross-sectional view illustrating part of a protected sensor constructed using a sensor anchoring device or another implantable graft or implantable device, in accordance with an additional embodiment of the present invention.

Reference is now made to FIG. 4 which is a schematic cross-sectional view illustrating part of a protected sensor constructed using a sensor anchoring device, or a sensor positioner, or an implantable graft, or an implantable device, in accordance with an additional embodiment of the present invention. The protected sensor 80 includes a sensor unit 82, an anchor 88 (only a part of the anchor 88 is illustrated in FIG. 4), and a compliant member 87. The anchor 88 has an opening 88C passing therethrough. The opening 88C is slightly smaller than the sensor unit 82. The compliant member 87 is sealingly glued or otherwise sealingly attached (using any suitable attachment method known in the art) to a first surface 88A of the anchor 88 and the sensor unit 82 is sealingly glued or otherwise sealingly attached (using any suitable attachment method known in the art) to a second surface 88B of the anchor 88.

The compliant member 87 may be a thin membrane having a high compliance constructed as disclosed in detail hereinabove for the compliant members 20, 20A and 54B (of FIGS. 1, 2, and 3, respectively). The compliant member 87 may be sealingly attached to the first surface 88A of the anchor 88 by a suitable glue or by any other sealing material or any other suitable attachment method known in the art or disclosed hereinabove, to form a sealed chamber 90. The sealed chamber 90 is completely filled with the substantially non-compressible medium 24 as disclosed hereinabove.

The sensor unit 82 may include the recessed substrate layer 12, and the second layer 14 constructed and operative as disclosed in detail hereinabove for the sensor unit 82 of the protected sensors 10 and 30 (of FIGS. 1 and 2, respectively).

Figure 5:
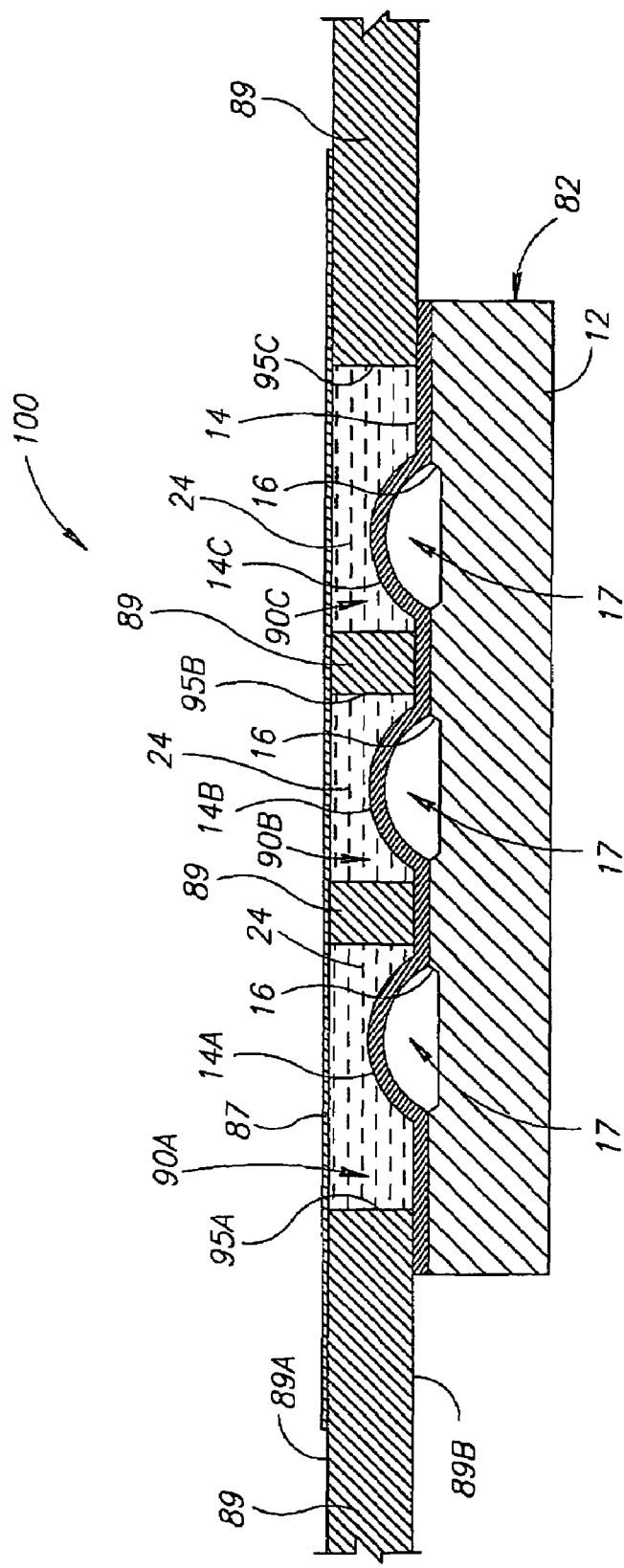
FIG. 5 is a schematic cross-sectional view illustrating part of a protected sensor having multiple sealed chambers constructed within a sensor anchoring device or implantable graft or implantable device, in accordance with another embodiment of the present invention.

Reference is now made to FIG. 5 which is a schematic cross-sectional view of part illustrating a protected sensor having multiple sealed chambers constructed within a sensor anchoring device or implantable graft or implantable device, in accordance with another embodiment of the present invention. The protected sensor 100 includes a sensor unit 82 as disclosed in detail hereinabove (with reference to FIG. 4), an anchor 89 (only a part of the anchor 89 is illustrated in FIG. 5), and a compliant member 87. The anchor 89 has a plurality of openings 95A, 95B and 95C passing therethrough. The compliant member 87 is sealingly glued or otherwise sealingly attached (using any suitable attachment method known in the art) to a first surface 89A of the anchor 89 and the sensor unit 82 is sealingly glued or otherwise sealingly attached (using any suitable attachment method known in the art) to a second surface 89B of the anchor 89.

The compliant member 87 may be a thin membrane having a high compliance constructed as disclosed in detail hereinabove for the compliant members 20, 20A and 54B (of FIGS. 1, 2, and 3, respectively). The compliant member 87 may be sealingly attached to the first surface 89A of the anchor 89 by a suitable glue or sealer, or by any other sealing material or any other suitable attachment method known in the art or disclosed hereinabove, to form a multiplicity of sealed chambers 90A, 90B and 90C. The sealed chamber 90 is completely filled with the substantially non-compressible medium 24 as disclosed hereinabove.

The sensor unit 82 may be constructed and operated as disclosed in detail hereinabove with reference to FIG. 4. It is noted that while the protected sensor 100 of FIG. 5 includes three sealed chambers (90A, 90B and 90C), the protected sensor 100 may be implemented having any suitable number of sealed chamber and any suitable number of vibratable members.

It is noted that, for the sake of clarity of illustration, the dimensions of the vibratable membranes 14A, 14B and 14C, and of the parts of the compliant member 87 overlying the chambers 90A90B and 90C, respectively do not necessarily represent the true dimensions of these parts and the ratio of their cross-sectional areas (such as, for example the ratio of the surface area of the vibratable membrane 14B to the area of the part of the compliant member 87 overlying the chamber 90B). Preferably, the surface area of the part of the compliant member overlying the chambers 90A, 90B and 90C are substantially greater than the surface area of the corresponding vibratable membranes 14A, 14B and 14C to allow proper sensor operation. It is noted that in all the other drawing figures, due to the schematic nature of the drawings, the scale and the ratio of the surface area of the part of the compliant member overlying a specific chamber to the surface area of the vibratable member or membrane included in that chamber may not necessarily be accurately represented.

It will be appreciated by those skilled in the art that the protected sensors of the present invention are not limited to sensors including a single vibratable member, or a single resonating sensor within a single sealed chamber. Thus, protected sensors including more than one sensor or more than one vibratable member within a sealed chamber are within the scope of the present invention.

For example, a protected sensor may be constructed in which there are multiple sealed chambers, each of the multiple sealed chambers may have more than one resonating sensors therewithin. Similarly, a protected sensor may be constructed in which there are multiple sealed chambers, each of the multiple sealed chambers may have more than one vibratable member therewithin. Additionally, a protected sensor may be constructed in which there is a single sealed chamber, in which more than one resonating sensors or more than one vibratable member may be disposed.

Figure 6:
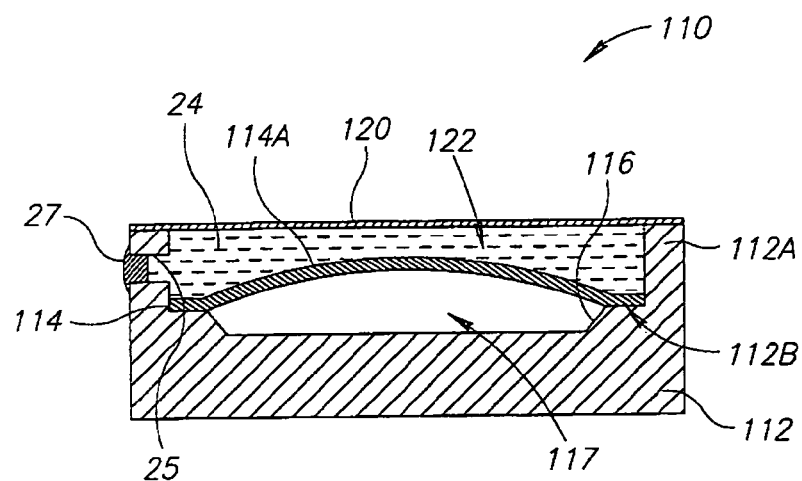
FIG. 6 is a schematic cross-sectional view illustrating a protected passive ultrasonic pressure sensor having a single vibratable membrane, in accordance with an embodiment of the present invention.

Reference is now made to FIG. 6 which is a schematic cross-sectional view illustrating a protected passive ultrasonic pressure sensor having a single vibratable membrane, in accordance with an embodiment of the present invention.

The sensor 110 may include a substrate 112, a second layer 114, a compliant member 120 and a substantially non-compressible medium 24 filling a sealed chamber 122. The second layer 114 may be glued or sealingly attached to a surface 112B of the substrate 112, as disclosed in detail hereinabove. The substrate 112 has a recess 116 formed therein. The substrate 112 has a ridge 112A protruding above the level of the surface 112B. The ridge 112A may (optionally) have an opening 25 passing therethrough. The opening 25 may be used for filling the chamber 122 with the medium 24, as disclosed in detail hereinafter. If the ridge 112A has one or more openings 25 formed therein, the opening(s) 25 may be closed after filling of the medium 24 by applying a suitable sealing material 27. The sealing material 27 may be any suitable sealing material known in the art, such as but not limited to, RTV, silicon based sealants, epoxy based sealing materials, or the like, as is disclosed in detail hereinafter.

The second layer 114 may be glued or sealingly attached to the surface 112B of the substrate 122 to form a sealed sensor unit chamber 117. A part of the second layer 114 that overlies the recess 116 forms a vibratable member 114A that may vibrate in response to mechanical waves (such as, for example, ultrasound waves) reaching the sensor 110. The sealed sensor unit chamber 117 may include a gas or a mixture of gasses having a pressure level therein, as disclosed hereinabove. The pressure level within the sealed sensor unit chamber 117 may be a zero pressure level (if the chamber 117 is evacuated of any gas) or may be a non-zero pressure level (if the chamber 117 includes a certain amount of a gas or gasses). The compliant member 120 may be attached or glued or sealingly attached (using any suitable attaching or sealing or gluing method known in the art) to the ridge 112A of the substrate 112 to form a chamber 122. The chamber 122 is preferably completely filled with the substantially non-compressible medium 24. The material composition of the parts of the sensor 110 may be similar to those disclosed hereinabove for other sensors.

It is noted that while the protected sensor 110 of FIG. 6 has a single sealed chamber 122 filled with the medium 24, a single sealed sensor unit chamber 117 and a single vibratable member 114A, other embodiments of the sensor may include more than one vibratable member, and/or more than one sealed sensor unit chamber, and/or more than one sealed chamber filed with the medium 24, as disclosed in detail hereinabove for other sensor embodiments.

It is noted that the anchor 88 (of FIG. 4) and the anchor 89 (of FIG. 5) may be any suitable part of any device (including, but not limited to, an implantable or an insertable device) to which the sensor unit 82 may be suitably attached in the configuration illustrated in FIG. 4, or in any other suitable configuration for forming a sealed chamber filled with a non-compressible medium. For example, the anchor 88 and the anchor 89 may be, but are not limited to, any suitable sensor support devices or sensor fixation devices, such as but not limited to the sensor supporting and/or sensor fixating devices disclosed in U.S. Pat. No. 6,331,163 to Kaplan. The anchor 88 and the anchor 89 may be, but are not limited to, any suitable part of a graft, a stent, an implantable electrode, an insertable electrode, a pacemaker, a defibrillator, a guide-wire, an endoscope, an endoscopic device, an autonomous endoscopic device or autonomous endoscopic capsule, a tethered endoscopic device or capsule, an implantable or an insertable drug or therapeutic substance releasing device or chip or pump, or any other implantable or insertable device known in the art, as disclosed in detail hereinabove.

Furthermore, if the protected sensors of the present invention are formed as a self contained protected sensor (such as, but not limited to, the protected sensors illustrated in FIGS. 1-3, and 6-9), the protected sensor may be suitably attached and/or glued to, and/or mounted on and/or affixed to and/or enclosed within any other suitable device which may be placed or disposed in the desired measurement environment. For example, the protected sensors of the present invention may be attached to a wall or any other internal part of a chemical or biochemical reactor (not shown) or to any measurement device or stirring device disposed in the reactor, or inside a valve or a tube or a holding tank, or the like.

Similarly, if the protected sensor is to be implanted in or inserted into an organism or animal or into a human patient, the protected sensor may be suitably attached and/or glued to, and/or mounted on and/or affixed to and/or enclosed within any suitable insertable or implantable device, including, but not limited to, a suitable graft, a stent, an implantable electrode, an insertable electrode, a pacemaker, a defibrillator, a guide-wire, an endoscope, an endoscopic device, an autonomous endoscopic device or autonomous endoscopic capsule, a tethered endoscopic device or a tethered capsule, an implantable or an insertable drug or therapeutic substance releasing device or chip or pump, or any other implantable or insertable device known in the art, and as disclosed in detail hereinabove.

Figure 7:
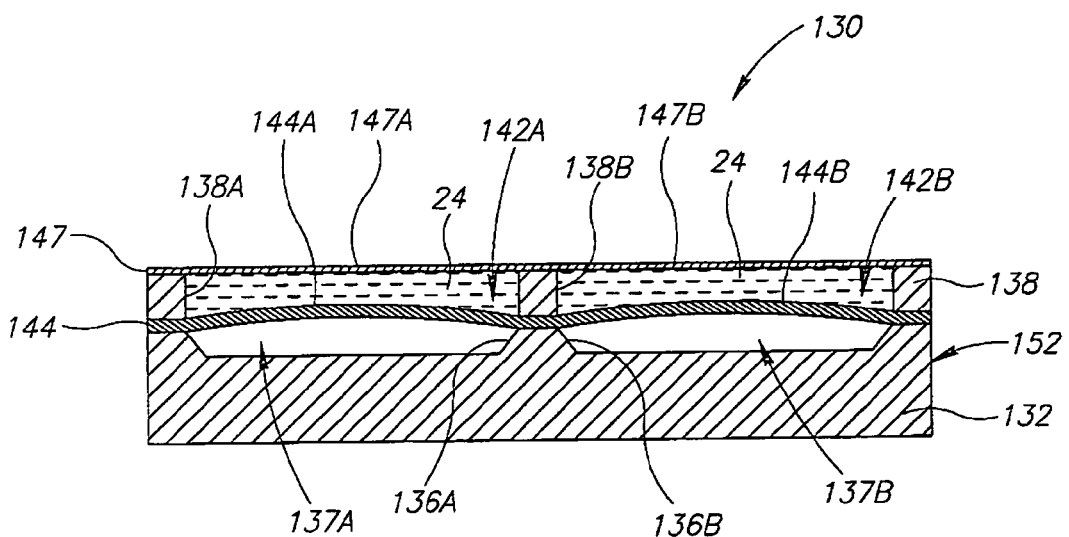
FIG. 7 is a schematic cross-sectional view illustrating a protected passive ultrasonic pressure sensor with multiple vibratable membranes having multiple sealed chambers formed within a spacer, in accordance with yet another embodiment of the present invention.

Reference is now made to FIG. 7 which is a schematic cross-sectional view illustrating a protected passive ultrasonic pressure sensor with multiple vibratable membranes having multiple sealed chambers formed within a spacer, in accordance with yet another embodiment of the present invention.

The protected sensor 130 may include a passive ultrasonic pressure sensor unit 152, a spacer member 138, a compliant member 147 and a substantially non-compressible medium 24. The spacer member 138 has two openings 138A and 138B formed therein. The sensor unit 152 includes a substrate 152 having two recesses 136A and 136B formed therein. The sensor unit 152 also includes a second layer 144 sealingly attached or bonded or glued to the substrate 132 to form two separate sealed sensor unit chambers 137A and 137B. The sealed sensor unit chambers 137A and 137B may be filled with a gas or a mixture of gases, or may have a vacuum therein as disclosed hereinabove. The parts of the layer 144 overlying the recesses 136A and 136B form two vibratable membranes 144A and 144B, respectively. The spacer member 138 may be sealingly attached or glued or bonded to the layer 144. The compliant member 147 may be suitably or sealingly attached or glued or bonded to the spacer member 138 to form two sealed chambers 142A and 142B. The sealed chambers 142A and 142B may, preferably, be completely filled with a substantially non-compressible medium 24, using any suitable filling method known in the art.

The part 147A of the compliant member 147 may protect the vibratable membrane 144A from deposition of extraneous material as disclosed in detail hereinabove. Similarly, the part 147B of the compliant member 147 may protect the vibratable membrane 144B from deposition of extraneous material.

It is noted that while the protected sensor 130 of FIG. 7 has two sealed chambers 142A and 142B filled with the medium 24, a single sealed sensor chamber 117 and a single vibratable member 114A, other embodiments of the sensor may include more than one vibratable member, and/or more than one sensor sealed chamber, and/or more than one sealed chamber filed with the medium 24, as disclosed in detail hereinabove for other sensor embodiments.

It is noted that different variations of components or functions of the illustrated embodiments are interchangeable between the different embodiments of the protected sensor assemblies as illustrated in FIGS. 1-8, and that many different permutations and variations thereof are possible and are included within the scope of the present invention.

It is noted that the protected sensors of the present invention, including but not limited to the sensors disclosed hereinabove and illustrated in FIGS. 1-8, may be constructed or assembled using various different methods. For example, turning briefly to FIG. 6, the sensor 110 may be made by first forming the substrate 112 and the recess 166 and opening 25 therein using any suitable photolithographic method known in the art (such as, but not limited to, standard lithographic masking, photoresist and wet etching methods applied to a silicon wafer or other suitable substrate, or by other suitable micromachining methods), the second layer 114 may then be glued or bonded or attached to the substrate layer 112 in a suitable pressure chamber to ensure the desired pressure level in the sensor sealed chamber 117.

The compliant member 120 may then be sealingly attached or glued or bonded to the ridge 112A of the substrate 112. The sensor 110 may then be placed in a suitable vacuum chamber (not shown) and allowing sufficient time for equilibration of pressure to form a suitable vacuum within the chamber 122 (which is not yet sealed at this stage). After the chamber 122 has a high vacuum therein, the sensor may be immersed in the medium 24 (for this vacuum assisted filling method the medium 24 should be a low vapor pressure liquid, such as but not limited to Dow Corning 710(R) Silicon Fluid disclosed hereinabove, or any other suitable low vapor pressure fluid or liquid known in the art) such as, for example, by introducing the medium 24 into the vacuum chamber to a suitable level such that the opening 25 is completely covered by the medium 24.

After, the opening 25 is covered by the medium 24, the pressure in the vacuum chamber in which the sensor 110 is disposed may be increased (for example, by opening the vacuum chamber to atmospheric pressure) as the pressure acting on the medium 24 disposed within the vacuum chamber is increased, the medium 24 will be forced into the empty space of the chamber 122 until the chamber 122 is completely filled with the medium 24. After the chamber 122 is filled with the medium 24, the sensor 110 may be cleaned (if necessary) and the opening 25 may be sealingly closed with the sealing material 27 to complete the sealing of the chamber 122. The sealing material 27 may be any suitable sealing material known in the art, as disclosed in detail hereinabove.

It is noted that it may also be possible, in accordance with another embodiment of the invention, to inject the medium 24 into the chamber 122 of the sensor 110 through the opening 25 by using a fine needle or any other suitable injecting device, which may be followed by application of the sealing material to seal the opening 25.

It is noted that the methods for filling the chamber 122 (or any other chamber of a protected sensor being used) with the medium 24 are not limited to using non-compressible liquids but may also be applied when using various types of gels. For examples when using gelatin it is possible to use the methods described hereinabove for filling the sensor by applying the gelatin while it is in a liquid fluid state prior to solidification by using a heated liquefied gelatin solution. In such cases it may be advantageous to warm the sensor that is being filled to a suitable temperature to prevent or delay solidification of the gel. When using hydrogels, time may be required for gelling, so it is possible to fill the chamber of the protected sensor before gelling occurs. In another example, it may be possible to use an alginate based gel (such as, for example, a liquid sodium alginate solution) and induce gel formation by adding calcium ions, as is known in the art.

It may also be possible to use other liquid compositions or liquid gel precursors that may form a gel after filling or injecting into the chamber 122 as disclosed hereinabove. For example, in accordance with an embodiment of the present invention it is possible to use a mixture of monomer(s) and a suitable catalyst and/or polymerizing agent and/or cross-linking agent which may chemically react to slowly produce a suitable gel. The mixture of the monomer and cross-linker may be injected or otherwise introduced into the chamber of the sensor (such as, but not limited to, the chamber 122 of the sensor 110) by any of the methods described hereinabove while still in the liquid state and may then polymerize to for the gel in the chamber.

In applications for non implanted sensors it may be possible to use gels such as polyacrylamide gels, as is known in the art. Such gels may be formed by polymerizing acrylamide or acrylamide derivative monomers using a polymerization catalyst or initiator (such as, for example, persulphate, or the like) and/or suitable cross-linking agents (for example bisacrylamide based cross-linkers). For applications using implantable sensors other, more biocompatible gels may be used, such as gelatin, or any other suitable bio-compatible hydrogel known in the art.

It is further noted that other different methods for constructing the protected sensor may be also used. Such methods may include methods in which the compliant member is attached to or formed on the protected sensor after the placement of the substantially non-compressible medium in the sensor. Briefly returning to FIG. 1, the sensor 10 may be constructed as follows. First the recessed substrate layer 12 may be attached to the second layer 14 in a vacuum chamber (not shown) to form the sensor unit 82 in a way similar to the way disclosed hereinabove for the sensor 110 of FIG. 6, or as disclosed in the above referenced co-pending U.S. patent application Ser. No. 10/828,218 to Girmonsky et al. After the sensor unit 82 is made, the spacer 18 may be attached or glued to the sensor unit 82 to form part of the chamber 22 (which at this stage is not yet a sealed chamber). The medium 24 may then be introduced into the formed part of the chamber 22 and the compliant member 20 may then be suitably sealingly attached or bonded to the spacer 18, using any attaching or gluing or bonding method known in the art, to seal the medium 24 and to complete the sealed chamber 22. This method may be applied when the medium 24 is a liquid or a gel. In cases where a gel is used, the gel may be introduced into the chamber 22 in a pre-gelled liquid form or as a monomer/cross-linker mixture as disclosed hereinabove.

Yet another method for constructing the protected sensor (described, by way of example, with respect to the sensor 10 of FIG. 6, but generally applicable to many of the other sensors disclosed and illustrated herein) may use chemical vapor deposition methods (or possibly other different methods known in the art to directly form and attache a compliant member to the sensor unit. Turning again to FIG. 1, the sensor 10 may also be constructed as follows. First the recessed substrate layer 12 may be attached to the second layer 14 in a vacuum chamber (not shown) to form the sensor unit 82 in a way similar to the way disclosed hereinabove. After the sensor unit 82 is made, the spacer 18 may be attached or glued to the sensor unit 82 to form part of the chamber 22 (which at this stage is not yet a sealed chamber). The medium 24 may then be introduced into the formed (yet open) part of the chamber 22. The compliant member 20 may then be directly deposited on the medium 24 and on the spacer 18 by forming the compliant member in-situ using a suitable chemical vapor deposition (CVD) method. For example, if the compliant member 20 is to be made from Parylene®C, a suitable layer of Parylene®C may be sealingly deposited or formed upon the medium 24 and the spacer 18 using standard CVD methods. In this case, the layer of Parylene®C formed over the substantially non-compressible medium 24 and attached to the upper surface of the spacer 18 comprises the compliant member 20. In such a case, if the CVD is performed below atmospheric pressure, the medium used in the sealed chamber must have a low vapor pressure.

It is noted that the different methods disclosed for constructing the protected sensors may in principle be applied to construct any of the protected sensors disclosed hereinabove and illustrated in the drawing figures with suitable modifications. For example, if the chamber 22 of sensor 10 of FIG. 1 needs to be to be filled with the medium 24 through an opening, one or more openings (not shown) may be made in the spacer 18.

Similarly, suitable openings (not shown) may be made in the housing 34 of the protected sensor 30 (of FIG. 2) or in the housing 54 of the protected sensor 50 of FIG. 3) or in any other suitable part of the protected sensors disclosed herein in order to enable the introducing of the substantially non-compressible medium 24 into the relevant chamber(s) of the protected sensor that is being filled.

In accordance with another embodiment of the invention, one or more openings (not shown) suitable for introducing the medium 24 may (optionally) be formed in suitable parts of the anchoring members 88 and/or 89 or in the sensor unit 82 to allow filling of the medium 24 therethrough. Such openings may be sealed by a sealing material after the filling is completed, as disclosed in detail with respect to the opening 25 of the sensor 110 of FIG. 6). It is therefore noted that if the substantially non-compressible medium is introduced into the sealed chamber of the protected sensor of the present invention through one or more openings, such an opening or such openings (not shown) may be formed in any selected or desired part of the sensor, such as, but not limited to, the sensor's housing or the sensor anchoring device (if user) or the spacer (if used) or through any suitable parts of the body of the sensor unit used. Such openings may be located at positions that will not compromise the sensor's operation as will be clear to the person skilled in the art.

Furthermore, if the protected sensor includes multiple sealed chambers (such as, for example, the chambers 90A, 90B and 90C of the protected sensor 100 of FIG. 5) additional openings (not shown) may have to be made in suitable parts of the sensor or sensor unit or spacer or anchoring device if needed.

It will be appreciated by those skilled in the art that the different methods disclosed herein for assembling or constructing the protected sensors of the invention, are given by way of example only, are not obligatory, and that other different methods of construction and/or assembly and or filling of the disclosed protected sensors my be used, as is known in the art. Such methods may include, but are not limited to, any suitable lithographic methods, etching methods, masking methods, semiconductor manufacturing methods, micromachining methods, imprinting methods, embossing methods, printing methods, layer forming methods, chemical vapor deposition methods, bonding methods, gluing methods, sealing methods, and the like.

It will be appreciated by those skilled in the art that the embodiments of the protected sensor described hereinabove and illustrated in FIG. 4 is not limited to the forms of sensor anchors or sensor fixation devices or stent parts shown above or in U.S. Pat. No. 6,331,163 to Kaplan. Rather, many different modifications of the protected sensor of the invention may be implemented by those skilled in the art. For example, a non-limiting list of possible implementations may include implementations in which the anchor 88 may be part of an implantable graft (for example a tube-like Gortex® graft, as is known in the art), or may be part of an implantable electrode of a pacemaker device or a defibrillator, or of any other suitable device which may be implanted in a blood vessel, or in any other part of a cardiovascular system, or intra-cranially, or within any of the ventricles of the brain, or in the central canal of the spinal cord, or in the heart, or in any other body cavity or lumen thereof, as is known in the art.

Reference is now made to FIG. 8 which is a schematic part cross-sectional diagram illustrating a generalized form of a protected resonating sensor in accordance with an embodiment of the present invention.

The protected sensor 180 of FIG. 8 includes a resonating sensor unit 5, a spacer 18, a compliant member 20 and a non-compressible medium 24. The resonating sensor unit 5 may be any type of resonating sensor known in the art which has one or more resonators or resonating parts exposed to a measurement environment or medium, such as, but not limited to, any of the resonating sensors disclosed hereinabove or known in the art. The resonator part 5A of the resonating sensor unit 5 schematically represents the part of the resonator (or resonators) of the resonating sensor unit 5 which would have been exposed to the measurement environment or medium in a non-protected resonating sensor unit 5.

The protected sensor 180 may include a spacer 18 suitably sealingly attached or glued to the sensor 5 as disclosed in detail hereinabove for the spacer 18 of FIG. 1. The protected sensor 180 may also include a compliant member 20 as disclosed in detail hereinabove for the sensor 10 of FIG. 1. The compliant member 20 is suitably sealingly attached to the spacer 18 to form a sealed chamber 102. The sealed chamber 102 is completely filled with a non-compressible medium 24 as described in detail hereinabove for the sensors 10, 30 and 80 (of FIGS. 1, 2 and 4, respectively).

The physical variable to be measured by the protected sensor 180 (such as, but not limited to, pressure, temperature or the like) is transmitted with minimal attenuation through the compliant member 20 and the non-compressible medium 24 to the part 5A of the resonating sensor unit 5, as disclosed in detail for the other passive ultrasonic sensors disclosed hereinabove. The compliant member 20 and the spacer 18 prevent the deposition of substance(s) or cell(s) or tissue(s) or other undesirable extraneous material from entering the sealed chamber 102 and from being deposited on or otherwise attached to the part 5A of the resonating sensor unit 5. The resonating part or parts of the sensor unit 5 (not shown in detail in FIG. 8) are thus protected from any such substance(s) or cell(s) or tissue(s) or other undesirable extraneous material found in the measurement environment or measurement medium which may improve the ability of the protected sensor 180 to maintain stability and accuracy of measurement over time.

It is noted that while in the embodiment of the protected sensor 80 illustrated in FIG. 5, the sealed chamber 102 including the medium 24 is constructed by using the spacer 18, it may be possible, in accordance with another embodiment of the protected sensor, to attach the compliant member 20 to a suitably formed part (not shown) of the sensor unit 5, such as a raised circumferential ridge (similar, but not necessarily identical to the ridge 112A of the sensor 110 of FIG. 6) formed as part of the sensor unit 5.

It is noted that in cases in which the sensor unit 5 is a resonating sensor for sensing the concentration of a chemical species in the measurement medium, the compliant member 20 and the non-compressible medium 24 should be carefully selected such that the compliant member 20 is made from a material which is suitably permeable to the chemical species being measured and that the non compressible medium 24 is selected such that the chemical species to be measured may be capable of diffusing in the selected medium 24, or may be capable of being transported through the medium 24 (for example, by including in the medium 24 a suitable transporter species or transporting molecule which is compatible with the medium 24, as is known in the art) to reach the part of the sensor unit 5 (possibly included in the part 5A of the sensor unit 5) which is sensitive to the concentration of the chemical species being measured.

It will be appreciated by those skilled in the art that the protected pressure sensors of the present invention are not limited to using only the type of compliant members disclosed hereinabove. Rather, the protected pressure sensors of the present invention may also be implemented by using differently configured compliant members. Such mechanically compliant members may be configured or shaped in many different ways (as is known in the art) to enable the efficient transmission of pressure from the region of measurement to the vibratable membranes or vibratable members of the sensor used. The compliant member also has to be sufficiently compliant so as not to substantially intererfere with the pressure waves of the vibrating vibratable member or membrane which may result in loss of quality factor.

Figure 9:
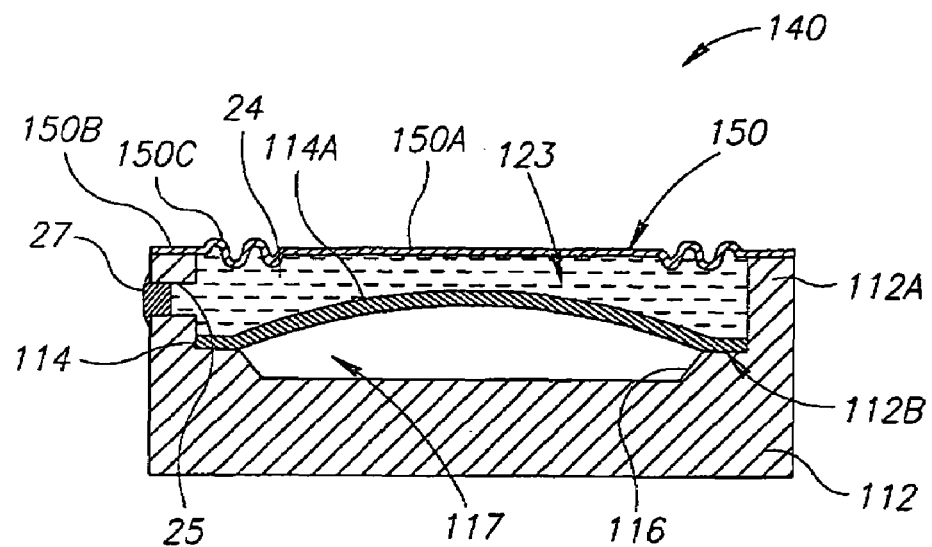
FIG. 9 is a schematic cross-sectional diagram illustrating a protected pressure sensor including a mechanically compliant member having a corrugated portion, in accordance with an embodiment of the present invention.

Reference is now made to FIG. 9 which is a schematic cross-sectional diagram illustrating a protected pressure sensor including a compliant member having a corrugated portion, in accordance with an embodiment of the present invention; and The pressure sensor 140 of FIG. 9 is similar but not identical to the pressure sensor 110 of FIG. 6. The substrate 112, the ridge 112A, the opening(s) 25, the sealing material 27, the second layer 114, the surface 112B, the surface 114A, and the substantially non-compressible medium 24 may be constructed as described in FIG. 6. However, while the sensor 110 of FIG. 6 has a compliant member 120 sealingly attached to the ridge 112A, to form the sealed chamber 122, the sensor 140 has a compliant member 150 sealingly attached to the ridge 112A to form a sealed chamber 123.

The compliant member 150 of FIG. 9 is different than the compliant member 120 of FIG. 6. The compliant member 150 of FIG. 9 is a mechanically compliant member including a first flat portion 150A, a second flat portion 150B and a corrugated portion 150C. The second flat portion 150B may be sealingly attached or glued to the ridge 112A of the substrate 112 to form a sealed chamber 123 which may be filled with the substantially non compressible medium 24 (such as, for example a substantially liquid or gel or hydrogel) as disclosed in detail hereinabove for the sensor 110. Preferably, (but not obligatorily) the first flat portion 150A, the second flat portion 150B and the corrugated portion 150C are contiguous parts of the compliant member 150. The corrugated portion 150C allows the first portion 150A to move in order to communicate the pressure outside the sensor 140 to the medium 24 disposed within the chamber 123 and to the vibratable member 114A, and to communicate the pressure waves from the vibrating member (or vibrating membrane) to the outside medium disposed in the measurement environment.

Figure 10:
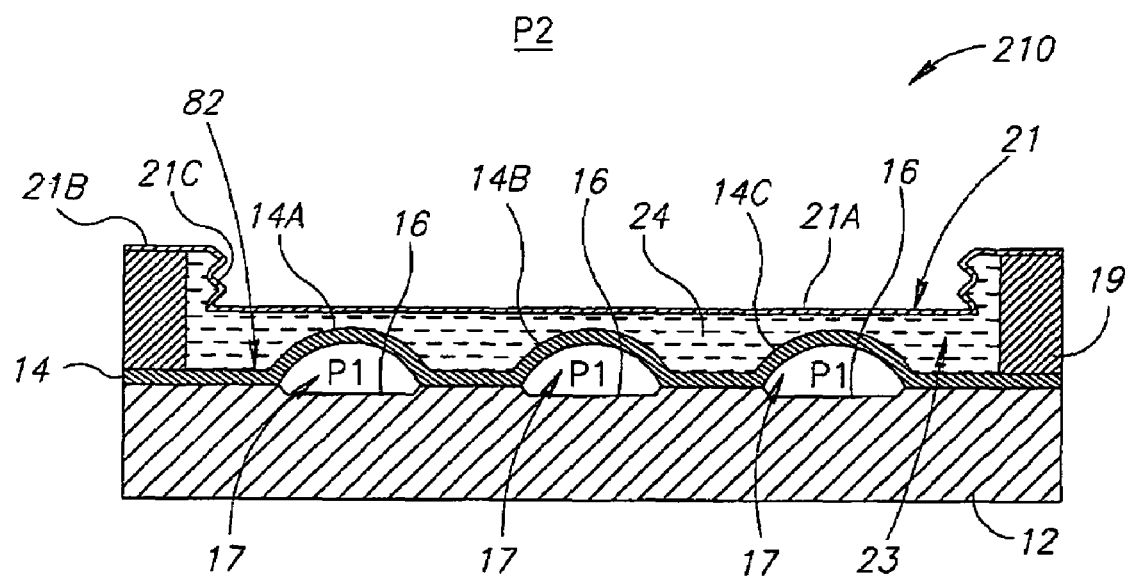
FIG. 10 is a schematic cross-sectional diagram illustrating a protected pressure sensor including a mechanically compliant member having a corrugated portion, in accordance with another embodiment of the present invention.

FIG. 10 is a schematic cross-sectional diagram illustrating a protected pressure sensor including a mechanically compliant member having a corrugated portion, in accordance with another embodiment of the present invention.

The sensor 210 of FIG. 10 is functionally similar but not structurally identical to the sensor 10 of FIG. 1. Like components of the sensors 10 and 210 are labeled with like reference numerals. The sensor 210 includes a compliant member 21. The compliant member 21 of FIG. 10 is different than the compliant member 20 of FIG. 1. The compliant member 21 of FIG. 10 is a mechanically compliant member including a first flat portion 21A, a second flat portion 21B and a corrugated portion 21C. The second flat portion 21B may be sealingly attached or glued to a spacer 19. The spacer 19 may be sealingly attached or glued to the substrate layer 12 (as disclosed in detail for the spacer 18 of FIG. 1 hereinabove) to form a sealed chamber 23 which may be filled with the substantially non compressible medium 24 (such as, for example a substantially liquid or gel or hydrogel) as disclosed in detail hereinabove for the sensor 110. Preferably, (but not obligatorily) the first flat portion 21A, the second flat portion 211B and the corrugated portion 21C are contiguous parts of the compliant member 21. The corrugated portion 21C allows the first portion 21A to move in order to communicate the pressure outside the sensor 210 to the medium 24 disposed within the chamber 23 and to the vibratable membranes 14A, 14B and 14C of the sensor 210. The corrugated portion 21C also allows the pressure waves of the vibratable membranes 14A, 14B and 14C to be communicates to the medium in the measurement environment outside of the protected sensor.

The sensor 210 includes a spacer 19. The dimensions of the spacer 19 (of FIG. 10) may be different than the dimensions the spacer 18 (of FIG. 1) or may be identical to the dimensions of the spacer 18 (of FIG. 1), depending, inter alia, on the chosen dimensions of the compliant member 21.

It is also noted that the various parts and components of the drawing Figures (FIGS. 1-10) are not drawn to scale and the dimensions and shapes are drawn for illustrative purposes only (for the sake of clarity of illustration) and may not represent the actual dimensions of the various illustrated components. For example, the curvature of the vibratable membranes 14A, 14B and 14C of the second layer 14 (of FIG. 1) is greatly exaggerated (for illustrative purposes) relative to the actual curvature of the vibratable membranes of actual sensors.

It is further noted that while the particular examples of the sensors disclosed hereinabove and illustrated in FIGS. 1-10 are adapted for pressure measurements, the protected sensors of the present invention may be also used as temperature sensors as is known in the art and as disclosed hereinabove. It may generally be also possible to use the protected sensors of the present invention for determination of other physical parameters within a measurement environment, if the measured parameters influence the resonance frequency of the vibratable part(s) or vibratable membrane(s) of the sensor.

It is further noted that while the sensors disclosed hereinabove and illustrated in the drawing figures are implemented as sensors having a plurality of vibratable membranes (multi-membrane sensors), the protected sensors of the present invention may also be implemented as sensors having a single vibratable membrane or a single vibratable part such as, but not limited to, the sensors disclosed, inter alia, in U.S. Pat. Nos. 5,619,997, 5,989,190 and 6,083,165 to Kaplan, or any other sensors known in the art. All such sensors may be implemented as protected sensors by suitable use of a compliant member and a non-compressible medium to form a sealed chamber filled with the non-compressible medium in which the non-compressible medium transmits the physical variable to be measured to the vibratable part of the sensor or to a suitable coupler coupled to the vibratable part.

It will be appreciated by those skilled in the art that the protected sensors of the present invention may be used for determining the value of a physical variable by using various different measurement methods. For example, the resonance frequency of the vibratable part(s) or the vibratable membrane(s) of the protected sensors disclosed hereinabove may be determined by using a continuous beam, or a pulsed beam, or a chirped beam of ultrasound for interrogating the protected sensors of the present invention and by measuring either the absorption of the energy of the exciting beam by the sensor, or the ultrasonic signal emitted by or returned from the sensor as is known in the art. Methods and systems for performing such measurement of the resonance frequency of passive sensors are disclosed in detail in U.S. Pat. Nos. 5,619, 997, 5,989,190 and 6,083,165, and 6,331,163 to Kaplan, and in co-pending U.S. patent application Ser. No. 10/828,218 to Girmonsky et al.

It is, however, noted that the method for protecting resonating sensors disclosed hereinabove is not limited for passive ultrasonic sensors disclosed hereinabove or to any particular measurement method disclosed hereinabove, but may be applied to any type of measurement method suitable for use with any type of resonating sensors, such as but not limited to, passive resonating sensors, active resonating sensors, optically interrogated active or passive resonating sensors, capacitive resonating sensors, or any other resonating sensor known in the art which has at least part of its resonating structure exposed to the measurement environment or medium, as long as they are interrogated by a sonic or ultrasonic beam.

It is further noted that during the construction of the protected sensors of the present invention (such as, for example, the sealed chamber 22 of the protected sensor 10) when the sealed chamber is filled with the medium 24 and sealed, care should be taken to avoid the trapping of any bubbles of gas or air in the sealed chamber. While it may still be possible to use a protected sensor containing such bubbles or gas filled spaces for performing measurements (depending, inter alia, on the size and cross-sectional area of such bubbles or gas filed spaces), such bubbles or any amount of gas or air trapped in the non-compressible medium 24 may undesirably affect or degrade the performance of the protected sensor because it introduces a compressible part (the gas in the space or a bubble containing a gas or gases) into the medium in the sealed chamber which may affect the actual pressure experienced by the vibratable membranes (such as, for example, the vibratable membranes 14A, 14B and 14C of the sensor unit 82) of the protected sensor, which may in turn introduce a certain measurement error. Additionally, gas bubbles trapped in the medium 24 contained within the sealed chamber may reflect or scatter part of the interrogating ultrasound beam, which may also undesirably affect the sensor's performance or the measurement system's performance.

Furthermore, the protected sensors of the present invention and parts thereof may be constructed of multilayered materials. For example, any of the recessed substrates, spacers, housings, and anchoring devices used in the construction of any of the protected sensors disclosed herein and illustrated in the drawings may (optionally) be formed as a multi-layered structure comprising more than one layer of material. Moreover, if such multi-layered structures are used in a part of the protected sensor, some of the layers may or may not include the same materials.

Moreover, while the examples disclosed hereinabove may use certain exemplary gel types for implementing the protected sensors of the invention, many other types of gels may also be used. For example, other types of gels may be used in implementing the protected sensors of the present invention, such as, but not limited to, polyvinyl alcohol (PVAL) based gels, polyvinylpyrrolidone (PVP) based gels, polyethylene oxide (PEO) based gels, polyvinylmethyl ester (PVME) based gels, polyacrylamide (PAAM) based gels, or any other type of suitable gel or hydrogel known in the art.

It is noted that when the selected gel forming method includes the polymerization of a mixture containing suitable gel forming monomers (with or without cross-linking agents), the polymerization may be induced by any suitable method known in the art. For example one possible method of forming a gel is adding a polymerization initiating agent to a solution containing a monomer and (optionally a cross-linking agent). The polymerization initiating agent may be a suitable free-radical forming agent, such as, but not limited to, potassium persulphate in the case of using polyacrylamide forming monomers, or any other suitable polymerization initiating compound known in the art). However, It may also be possible to use other methods for initiating a polymerization of a monomer (or a mixture of different monomers) such as irradiating a suitable monomer(s) solution (with or without suitable cross-linking agents or other copolymers) with light having a suitable wavelength (such as, but not limited ultraviolet light, or light having other suitable wavelengths, or by using other types of ionizing radiation or other types of radiation. However, any other suitable method for initiating polymerization known in the art may be used in forming the gels included in the protected sensors of the present invention. It is further noted that many other types of gels and gel forming methods may be used in the present invention, as is known in the art. Such gels may include but are not limited to, agar, agarose, alginates, gelatin, various polysaccharide based gels, protein based gels, synthetic polymer based gels (including cross-linked and non-cross-linked polymer based gels), and the like.

It is further noted that the protected sensors of the present invention and parts thereof may be constructed of multilayered materials. For example any of the recessed substrates, spacers, housings, and anchoring devices used in the construction of any of the protected sensors disclosed herein and illustrated in the drawings may (optionally) be a multi-layered structure comprising more than one layer of material. Furthermore, if such multi-layered structures are used in a part of the protected sensor, some of the layers may or may not include the same materials.

Furthermore, it is noted that the vibratable members (or resonating members) of the sensor units used in the protected sensors of the present invention may have many different shapes and/or geometries. For example, the vibratable membranes of the passive ultrasonic sensor units disclosed hereinabove (such as, but not limited to, the vibratable membranes of the sensors 10, 30, 50, 80, 100, 110, 130, 140, 180, 185, 190, 210, 250, 260, 270, 280, 290 and 300) may have a circular shape, a rectangular shape, a polygonal shape, or any other shape known in the art and suitable for a vibratable resonator, as is known in the art. For example, the sensor illustrated in FIG. 2 of co-pending U.S. patent application Ser. No. 10/828,218 to Girmonsky et al., has multiple vibratable membranes having a rectangular shape, but any other suitable vibratable membrane shapes may be used.

It is further noted that, while all the embodiments of the protected sensor of the present invention are described and illustrated as having a single contiguous compliant member, in accordance with another embodiment of the present invention the sensors may be modified to include two or more separate compliant members suitably and sealingly attached to the sensor unit(s) or to the housing of the protected sensor (s) or to the anchor or support to which the sensor unit(s) are attached.

It will be appreciated by those skilled in the art that the methods disclosed hereinabove for protecting a sensor and for constructing protected sensors (including, but not limited to, the sensors having compliant member(s) disclosed herein and the open gel protected sensors disclosed herein) are not limited to the various exemplary embodiments disclosed and illustrated herein, and may be applied to other different sensors having vibratable parts or vibratable members. For example, the methods disclosed hereinabove may be applied to the passive ultrasonic sensors described in U.S. Pat. Nos. 5,989,190 and 6,083,165 to Kaplan, to construct protected passive ultrasonic sensors that are considered to be within the scope and spirit of the present invention. Thus, the vibratable member(s) or vibratable membrane(s) of the sensor unit(s) used for constructing the protected sensors of the present invention may be formed as a thin integral part of a recessed layer (such as, for example, the membrane 91 of the sensor 90 of FIG. 7 of U.S. Pat. No. 5,989,190 referenced above). Thus, the method disclosed herein of constructing protected sensors using resonating sensor unit(s), the substantially non-compressible medium and a compliant member, is a general method and may be generally applied to other suitable passive and active resonating sensors known in the art.

It is noted that while all the protected sensors disclosed hereinabove and illustrated in the drawings include one or more passive resonating sensor units, the protected sensors of the present invention (including, but not limited to, the sensors having compliant member(s) disclosed herein and the open gel protected sensors disclosed herein) are not limited to resonating sensor units only and may include additional types of sensor units. Thus, the protected sensors of the present invention may also include any other suitable type of sensor units known in the art. For example, in accordance with an embodiment of the present invention the protected sensor may include one or more resonating pressure sensor units as disclosed hereinabove and an additional non-resonating temperature sensor unit (not shown) of any suitable type known in the art. Such a temperature sensor unit may or may not be disposed within the chamber of the protected sensor. For example, if such a non resonating temperature sensor is included in a protected sensor of the type shown in FIG. 3, the additional temperature sensor unit may be disposed within the medium 24 in the sealed chamber 52, or alternatively may be suitably attached to the housing 54 such that it is disposed outside of the sealed chamber 52. Such non-resonating temperature sensor unit(s) (or any other type of non-resonating sensor unit(s) for measuring other physical or chemical parameters) may also be embedded in, or formed within, or included in, or suitably attached to the housing 54. Similarly, the open gel-protected sensors of the present invention may also include one or more non-resonating sensor units.

As may be appreciated by the person skilled in the art, many other types of combinations of resonating sensor units and non-resonating sensor units may thus be implemented in the protected sensors of the present invention The non-resonating sensor units of such combinations of sensor units may be configured to determine any desired physical or chemical parameter in the measurement environment, as is known in the art. Thus, protected sensors including such combinations of resonating and/or non-resonating sensor units are included within the scope and spirit of the present invention.

It is noted that in embodiments in which the protected sensors of the present invention are configured to be disposed in contact with blood (such as, but not limited to protected pressure sensors which are designed to be implanted in a blood vessel or in any other part of the cardiovascular system), the parts of the sensor which come into contact with blood are preferably made from hemocompatible materials or suitably coated with hemocompatible materials, as is known in the art. The use of hemocompatible materials may be advantageous by, inter alia, reducing or preventing blood clotting, blood cells' adhesion, or other adverse effects.

It is further noted that while the chambers 22 (FIG. 1), 32 (FIG. 2), 52 (FIG. 3), 90 (FIG. 4), 90A-90C (FIG. 5), 122 (FIG. 6), 142A and 142 (FIG. 7), 102 (FIG. 8), 123 (FIG. 9) and 23 (FIG. 10) are illustrated as sealed chambers, this is not obligatory. Thus, when the medium 24 filling the chambers 22, 32, 52, 90, 90A, 90B, 90C, 122, 142A, 142, 102, 123, and 23 is a gel or a hydrogel, the chambers 22, 32, 52, 90, 90A, 90B, 90C, 122, 142A, 142, 102, 123 and 23 may be open chambers (not shown in FIGS. 1-10), and need not obligatorily be completely sealed.

For example, if the compliant member 20 of the sensor 10 is glued or attached to the spacer 18 after casting a gel 24 into the sensor, the compliant member 20 need not fully and completely seal the formed chamber 22, because the sensor's performance does not substantially depend on the chamber 22 being a sealed chamber. Thus, the compliant member 20 may be non-sealingly attached to the spacer 18.

In another example, when the chamber 122 of the sensor 110 of FIG. 6 is filled with a gel through the opening 25 (as disclosed in detail hereinabove), the opening 25 may be left open (by not closing it with the sealing material 27 as described hereinabove with respect to FIG. 6). After gelling is completed, the solidified gel will stay in the chamber 122 even though the opening 25 stays open. Alternatively, when a gel is used within the chamber 122, the chamber 122 may also be sealed by closing the opening 25 with the sealing material 27 as disclosed in detail hereinabove for a liquid filled chamber.

Similarly, when using a gel as the medium 24, one or more suitable openings (not shown) may be made in any suitable parts of the other sensors illustrated above and such openings may be left open without substantially affecting the sensor's operation as a resonator. Such openings may be made in any suitable part of the sensor, including but not limited to, in the substrate layer 12 and/or in the layer 14 and/or in the spacer 18 and/or the compliant member 20 (of FIGS. 1 and 2), in the housing 34 and/or the compliant member 20A (FIG. 2), in the housing 54 and/or in the substrate layers 62 and/or 72, and/or in the layers 64 and/or 74 and/or the compliant member 54B (FIG. 3), in the substrate layer 82 and/or in the layer 14, and/or the anchor 88 and/or the compliant member 87 (of FIG. 4), in the in the substrate 82 and/or in the layer 14, and/or the anchor 89 and/or the compliant member 87 (of FIG. 5), in the substrate layer 112 and/or the layer 114 and/or the compliant member 120 (of FIG. 6), in the substrate 132 and/or the layer 144 and/or the spacer 138 and/or the compliant member 147 (of FIG. 7), in the sensor 5, and/or spacer 18 and/or the compliant member 20 (of FIG. 8), in the substrate 112 and/or the ridge 112A and/or the layer 114, and/or the compliant member 150 (of FIG. 9), in the substrate layer 12 and/or the layer 14 and/or the spacer 19 and/or the compliant member 21 (of FIG. 10).

However, since the particular examples of the sensors illustrated hereinabove are given by way of example only and many other sensor configurations are possible within the scope of the present invention, such an opening or openings may be formed in any other suitable part of the protected sensors of the present invention and/or between different parts of a sensor (such as, for example, by forming an opening between the spacer 18 and the substrate layer 12 of the sensor 10 by non-sealingly or incompletely attaching or gluing the spacer 18 to the substrate layer 12), depending, inter alia, on the resonating sensors' structure and configuration, the structure and configuration of the compliant member, and the presence and structure of spacer(s) or housing(s), anchors, or other sensor parts.

It is noted that while filling the sensors with the medium 24 through such openings (not shown) is possible (as disclosed in detail for the opening 25 of the sensor 110), this is not obligatory, and any other method for filling the sensors with the medium 24 (either a gel or a liquid) may be used as disclosed in detail hereinabove, or as is known in the art.

While the invention has been described with respect to a limited number of embodiments, it will be appreciated that many variations, permutations and modifications may be made to the structure, dimensions, material composition, and construction methods of the protected sensors of the present invention, and other numerous applications of the protected sensors of the present invention which are all considered to be within the scope and spirit of the present invention.

It is noted that the compliant members of the present invention (such as, for example, the compliant members 20, 20A, 21, 54B, 87, 120, 147 and 150 disclosed hereinabove) may be advantageous in protecting the medium 24 from mechanical damage or other types of damage during the sensor placement in the measurement environment. Furthermore, when the medium 24 is a liquid, the compliant members of the present invention seals the liquid within the sensor as shown in detail hereinabove and may prevent the liquid from exiting the sensor and from being removed or dispersed in the measurement environment by the liquid present in the measurement environment. However, it is also possible to construct a protected sensor without using a compliant member by using a suitable gel for covering the vibratable member(s) or any other resonating parts of the sensor or of any resonating sensor unit(s) included in the protected sensor.

Figure 11:
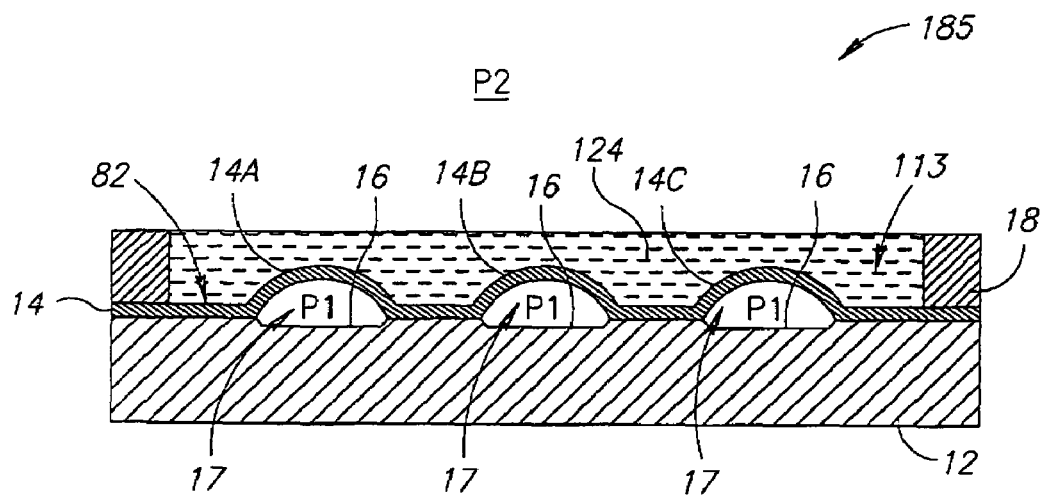
FIG. 11 is a schematic cross-sectional view illustrating a gel protected passive ultrasonic pressure sensor having multiple vibratable membranes, in accordance with an embodiment of the present invention.

Reference is now made to FIG. 11 which is a schematic cross-sectional view illustrating a gel protected passive ultrasonic pressure sensor having multiple vibratable membranes, in accordance with an embodiment of the present invention.

The sensor 185 may include the sensor unit 82 (of FIG. 1). The sensor unit 82 may be constructed as disclosed hereinabove in detail for the sensor 10 of FIG. 1. The sensor 185 may further include the spacer 18 attached to the sensor unit 82. The spacer 18 may be a rigid spacer as disclosed in detail hereinabove but may also be made as a non-rigid spacer made of any suitable material known in the art.

A body of gel 124 is disposed within an open chamber 113 defined by the second layer 14 of the sensor unit 82 and by the spacer 18. The gel 124 may be any type of suitable gel as disclosed hereinabove. For example the gel 124 may be gelatin, or any suitable type of lipogel or hydrogel, such as but not limited to, a polyacrylamide based gel as describe hereinabove and known in the art. It may also be possible to use any other suitable types of natural gels (such as, but not limited to, agar, agarose, or the like), or synthetic gels (such as, but not limited to, synthetic hydrogels), or any other type of suitable gel disclosed herein or known in the art. For open protected sensors of the present invention that are implantable sensors, the gel may preferably be a biocompatible gel. Similarly, if the implantable protected open sensor is to be exposed to blood, the gel may preferably be a hemocompatible gel, as is known in the art.

Furthermore, preferably, the composition or type of gel should be selected such that it would be substantially resistant to degradation or consumption by substances or chemicals or solvents or living cells or enzymes, or any other components present in the measurement environment to which the sensor is exposed. For example, if the protected sensor is disposed in a chemical reactor, the type of protecting gel should be selected to substantially resist degradation by any solvents or chemical reactants found within the reactor. Similarly, if the sensor is implanted in a body and is in contact with blood (or with other tissues), the gel may be a gel which is substantially resistant to degradation by blood enzymes of other blood components or other tissue components.

In accordance with an embodiment of the present invention, the gel 124 may be disposed in the open chamber 113 by casting a pre-gelled liquid into the open chamber 113. For example, a warmed liquid aqueous gelatin solution may be introduced into the chamber 113 and allowed to solidify as it cools to room temperature. In accordance with another embodiment of the invention, the chamber 113 may be filled with a liquid mixture containing suitable ingredients for forming a polymerized and/or crossed linked gel, and the mixture allowed to polymerize. For example, this method may be used for forming a polyacrylamide based gel (as described ion detail hereinabove) within the chamber 113, but any other type of suitable polymerizable monomers and or cross-linking compounds and initiating compounds and/or other gel precursors may be used to form other suitable type of gel in the chamber 113.

Preferably, the gel 124 is selected such that its acoustic impedance is close to the acoustic impedance of the medium (not shown) or tissue(s) (not shown) in the measurement environment to reduce the portion of the interrogating beam of ultrasound (or other acoustic beams, if used) reflected from the interface (not shown) between the gel 124 and the medium or tissue present in the measurement environment. However, this is not obligatory, and the acoustic impedance of the gel 124 need not be equal or very close to the acoustic impedance of the medium or tissue(s) in the measurement environment and some impedance mismatch may be acceptable depending, inter alia, on the signal to noise, the sensitivity of the system used to interrogate the sensor(s), the particular frequencies and intensities of the sonic beam used for interrogating the sensor(s), and the actual composition of the gel and/or of the measurement environment.

The gel 124 is in contact with the second layer 14 and completely covers the vibratable members 14A 14B and 14B. The gel 124 thus provides protection to the vibratable members 14A, 14B and 14C of the sensor unit 82 and prevents the deposition of extraneous material from the measurement environment on the vibratable members 14A, 14B and 14C or attachment It is noted that while the body of gel 124 of FIG. 11 is shown as completely filling the chamber 113 up to the top part of the spacer 18, this is not obligatory, and the gel 124 may only partially fill the chamber 113 as long as it completely covers the vibratable membranes 14A, 14B and 14C to prevent the changing of the resonance frequency(s) of the vibratable membranes 14A, 14B and 14C by accumulation of extraneous material from the measurement environment on the vibratable membranes 14A, 14B and 14C.

Figure 12:
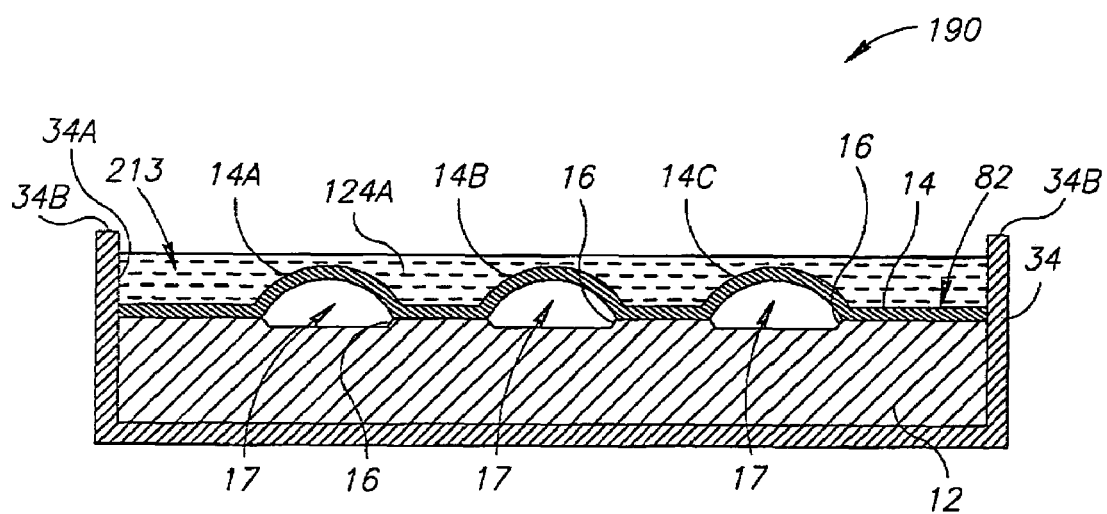
FIG. 12 is a schematic cross-sectional view illustrating a protected passive ultrasonic pressure sensor disposed in an open housing and protected by a gel, in accordance with another embodiment of the present invention.

Reference is now made to FIG. 12 which is a schematic cross-sectional view illustrating a protected passive ultrasonic pressure sensor disposed in an open housing and protected by a gel, in accordance with another embodiment of the present invention.

The protected sensor 190 includes the sensor unit 82 disclosed hereinabove (with reference to FIG. 11), a housing 34 as disclosed hereinabove and a body of gel 124A. The body of gel 124A is disposed in the open chamber 213 such that it covers the second layer 14 and is in contact (as seen in FIG. 12) with part of the surface 34A of the housing 34).

The gel 124A is similar to the gel 124 (FIG. 11) and may be composed as described hereinabove for the gel 124. The gel 124A may be disposed in the chamber 213 of the sensor 190 using any of the methods described hereinabove for placing the gel 124 in the chamber 113. It is noted that while the gel 124A is shown as only partially filling the chamber 213, it is also possible to dispose the gel 124 within the protected sensor 190 such that the gel 124A completely fills (not shown in FIG. 12) the chamber 213 and may even protrude beyond the rims 38B of the housing 34. For example the gel 124A may be disposed in the housing 34 such that its upper part forms a meniscus (not shown) and part of the upper surface of the gel 124 protrudes beyond the level of the rims 34B.

Figure 13:
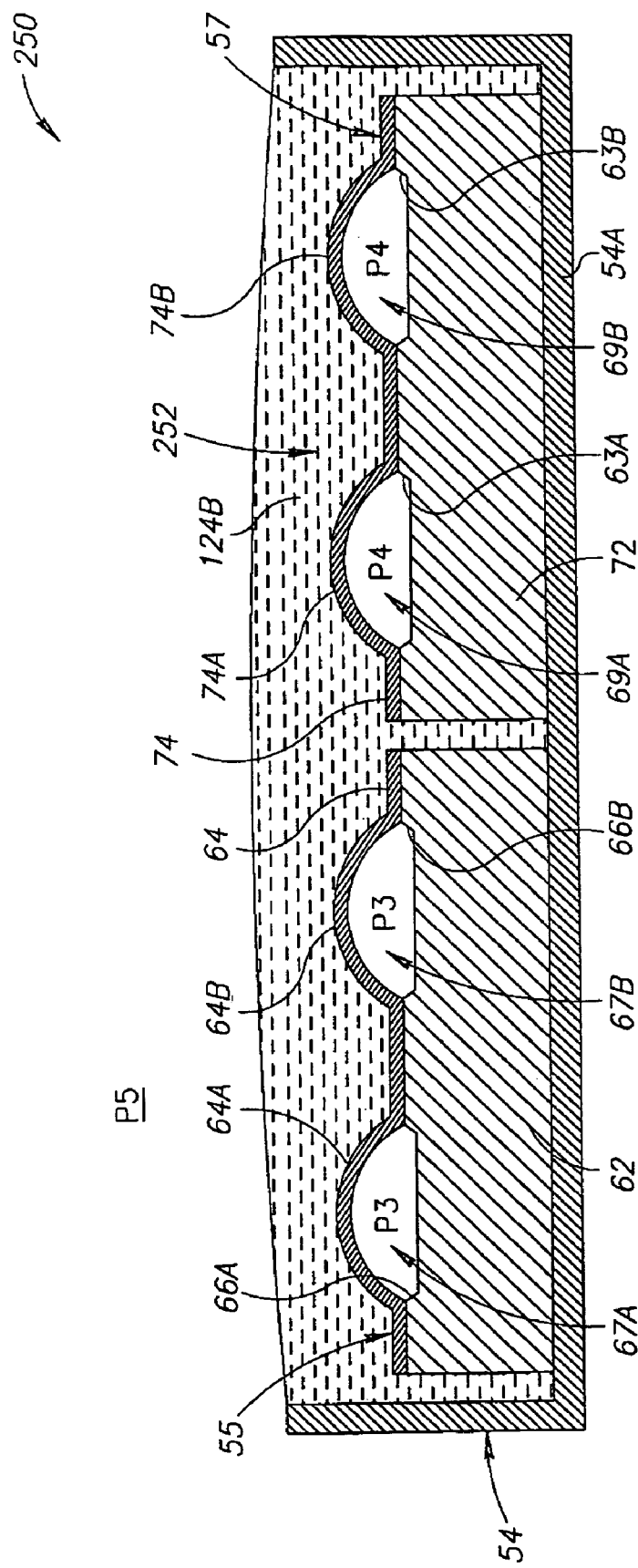
FIG. 13 is a schematic cross-sectional view illustrating a protected ultrasonic pressure sensor including two different passive ultrasonic sensor units disposed within a single protective housing and covered with a gel, in accordance with another embodiment of the present invention.

Reference is now made to FIG. 13 which is a schematic cross-sectional view illustrating a protected ultrasonic pressure sensor including two different passive ultrasonic sensor units disposed within a single protective housing and covered with a gel, in accordance with another embodiment of the present invention.

The sensor 250 of FIG. 13 is similar (but not identical) in structure to the sensor 50 (of FIG. 3), except that the sensor 250 does not include the compliant member 54B of the sensor 50. The sensor 250 includes the sensor units 55 and 57 attached to the housing 54. While the sensor 50 of FIG. 3 has a medium 24 (a liquid or a gel) sealed in a chamber 52, the sensor 250 of FIG. 13 includes a body of gel 124B. The sensor 250 does not have a sealed chamber like the sealed chamber 52 of FIG. 3. Instead, the sensor 250 has an open chamber 252 in which the body of gel 124B is disposed. The gel 124B protects the vibratable membranes 64A, 64B of the sensor unit 55 and the vibratable membranes 74A and 74B of the sensor unit 57 from deposition of extraneous materials found in the measurement environment as disclosed hereinabove. It is noted that the body of gel need not obligatorily fill the entire chamber 252 as shown in FIG. 13. Rather, the gel may only partially fill the chamber 252, as long as it is sufficiently thick to provide adequate protection to the vibratable membranes 64A, 64B, 74A and 74B.

The gel body 124B may be any of the gels described herein and may be disposed in the chamber 252 by any of the methods disclosed in detail hereinabove.

Figure 14:
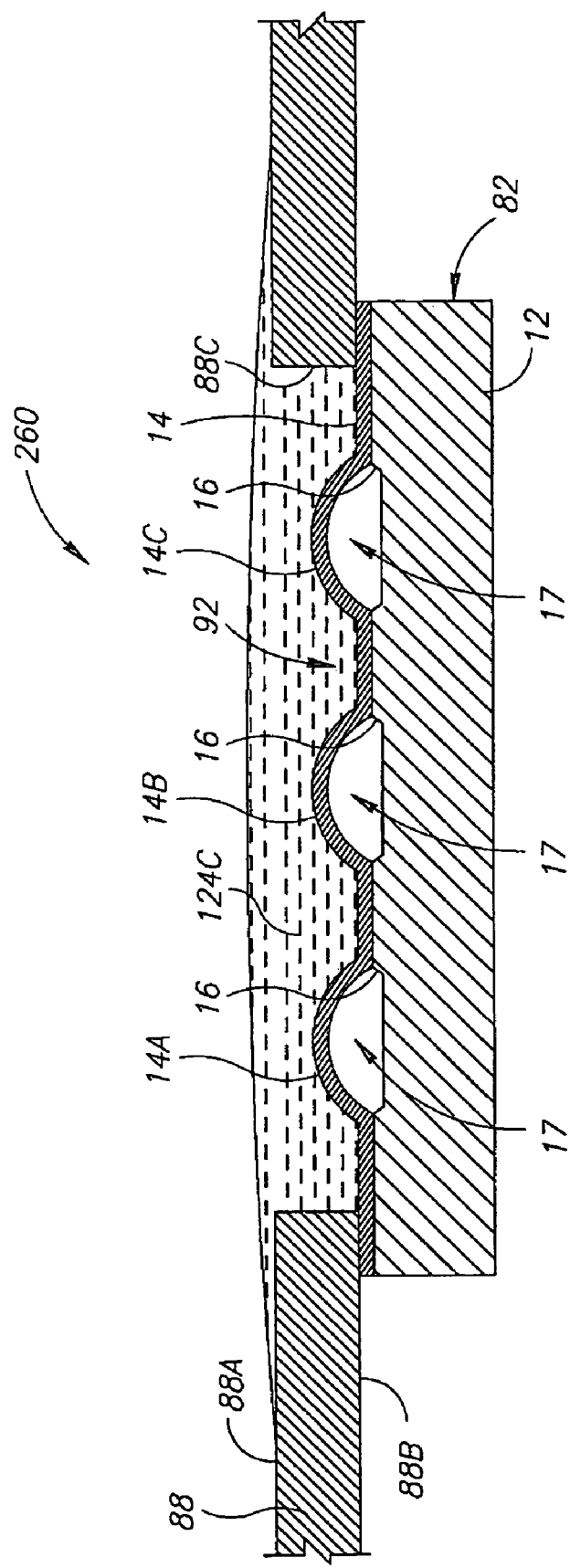
FIG. 14 is a schematic cross-sectional view illustrating part of an open gel-protected sensor constructed using a sensor anchoring device or an implantable graft or implantable device, in accordance with an additional embodiment of the present invention.

Reference is now made to FIG. 14 which is a schematic cross-sectional view illustrating part of an open gel-protected sensor constructed using a sensor anchoring device or an implantable graft or implantable device, in accordance with an additional embodiment of the present invention. The sensor 260 includes the sensor unit 82 (as disclosed in detail hereinabove and illustrated in FIG. 4). The sensor 260 also includes the anchor 80 (as disclosed in detail hereinabove and illustrated in FIG. 4). The sensor unit 82 is attached to the anchor 88 as disclosed in detail hereinabove. However, in contrast with the sensor 80 of FIG. 4, the sensor 260 does not include the compliant member 87 and the sealed chamber 90. Instead, the sensor 260 has a body of gel 124C that is disposed in the open chamber 92 as shown in FIG. 14. The body of gel may or may not cover part of the surface 88A of the anchor 88. While in the embodiment of the sensor illustrated in FIG. 14, the body of gel 124C also covers a portion of the surface 88A of the anchor 88, this is not obligatory, and the body gel may also be disposed in the open chamber 92 such that it is approximately at the same level (not shown in FIG. 14) with the plane defined by the surface 88A of the anchor 88. Alternatively, in accordance with another embodiment of the invention, the body of gel may only partially fill (not shown in FIG. 14) the open chamber 92, such that the level of the upper surface of the body of gel is below the level of the surface 88A while the gel still fully covers the vibratable membranes 14A, 14B and 14C of the sensor unit 82.

The gel body 124C may be any of the gels described herein and may be formed or disposed within the open chamber 92 by any of the methods disclosed in detail herein.

Figure 15:
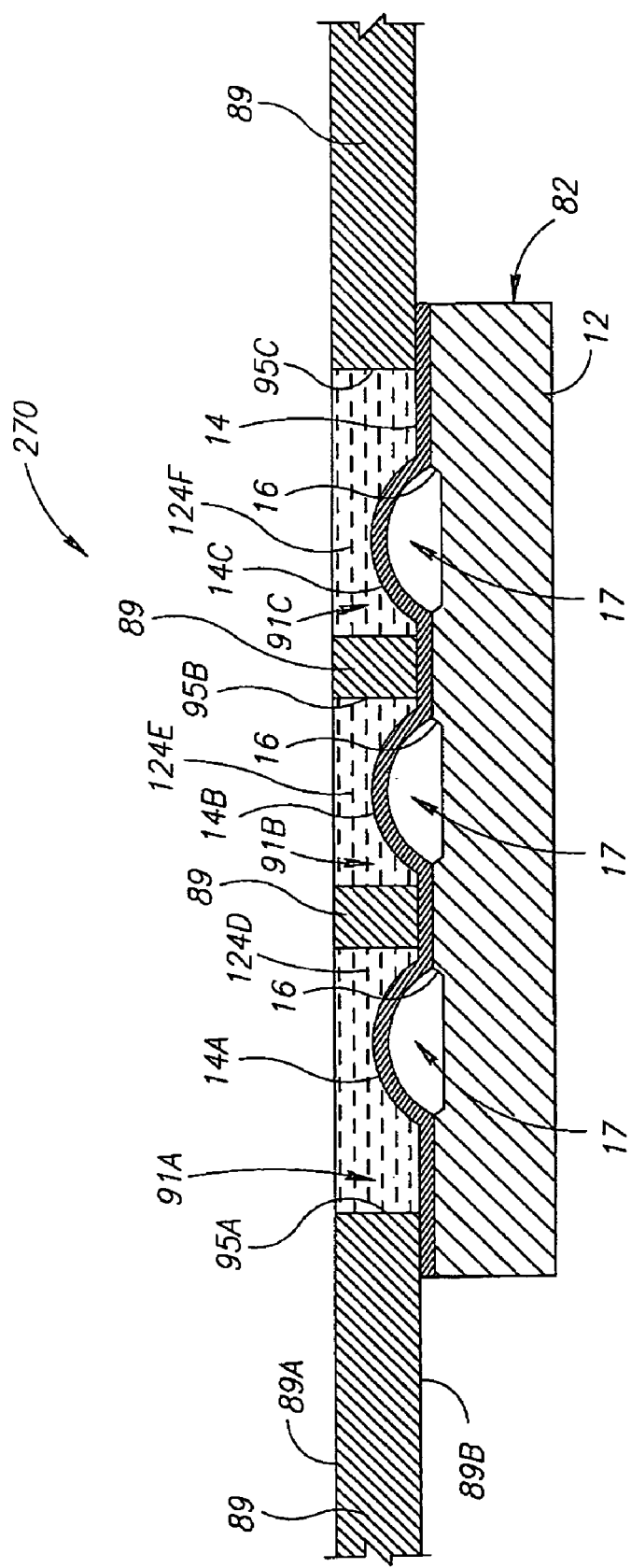
FIG. 15 is a schematic cross-sectional view illustrating part of a gel-protected sensor having multiple open gel-filled chambers and constructed within a sensor anchoring device or an implantable graft or an implantable device, in accordance with another embodiment of the present invention.

Reference is now made to FIG. 15, which is a schematic cross-sectional view illustrating part of a gel-protected sensor having multiple open gel-filled chambers and constructed within a sensor-anchoring device or an implantable graft or an implantable device, in accordance with another embodiment of the present invention. The sensor 270 includes the sensor unit 82 (as disclosed in detail hereinabove and illustrated in FIG. 5). The sensor 270 also includes the anchor 89 (as disclosed in detail hereinabove and illustrated in FIG. 5). The sensor unit 82 is attached to the anchor 89 as disclosed in detail hereinabove. However, in contrast with the sensor 100 of FIG. 5, the sensor 270 does not include the compliant member 87 and the sealed chambers 90A, 90B and 90C. Instead, the sensor 270 has three bodies of gel 124D, 124E and 124F that are disposed in open chambers 91A, 91B and 91C, respectively, as illustrated in FIG. 15.

The body of gel 124D is disposed in the open chamber 91A and overlies the vibratable membrane 14A. The body of gel 124E is disposed in the open chamber 91B and overlies the vibratable membrane 14B. The body of gel 124F is disposed in the open chamber 91C and overlies the vibratable membrane 14C. The bodies of gel 124D, 124E and 124F protect the vibratable membranes 14A, 14B and 124C, respectively, from deposition of extraneous materials thereupon from the measurement environment to prevent changes in the resonance frequencies of the vibratable members 14A, 14B and 14C.

It is noted that the level of the gel disposed in the chambers 91A, 91B and 91C need not obligatorily be flush with the plane of the surface 89A of the anchor 89 as illustrated in FIG. 15. Rather, in accordance with an embodiment of the invention, the level of any of the bodies of gel 124D, 124E and 124F within their respective chambers may be lower than the level of the surface 89A. Alternatively, in accordance with another embodiment of the invention (not shown in FIG. 15), a single body of gel may be disposed on the protected sensor 270 such that it completely fills all the chambers 91A, 911B and 91C and also covers part of the surface 89A of the anchor 89.

The gel bodies 124D, 124E and 124F may be any of the gels described herein and may be formed or disposed within the open chambers 91A, 91B and 91C by any of the methods disclosed in detail herein.

Figure 16:
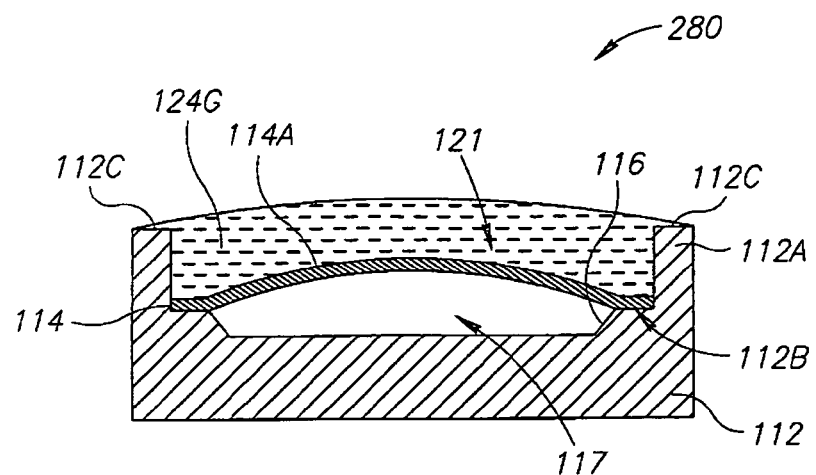
FIG. 16 is a schematic cross-sectional view illustrating an open gel-protected passive ultrasonic pressure sensor having a single vibratable membrane, in accordance with an embodiment of the present invention.

Reference is now made to FIG. 16 which is a schematic cross-sectional view illustrating an open gel-protected passive ultrasonic pressure sensor having a single vibratable membrane, in accordance with an embodiment of the present invention.

The sensor 280 of FIG. 16 is similar (but not identical) to the sensor 110 (of FIG. 6). The sensor 280 includes the substrate 112 and the ridge 112A thereof, the second layer 114 having a vibratable membrane 114A overlying the sealed chamber 117, as disclosed in detail hereinabove for the sensor 110 of FIG. 6. It is noted that the ridge 112A of FIG. 16 does not have the opening 25 of FIG. 6 since such an opening is not needed for filling the gel in the sensor. Furthermore, in contrast to the sensor 110, the sensor 280 of FIG. 16 does not include the compliant member 20 (of FIG. 6). The sensor 280 includes a body of gel 124G which is disposed within the open chamber 121. The body of gel 124G overlies the single vibratable membrane 114A. The body of gel 124G also overlies the surface 112C of the ridge 112A.

It is noted that the body of gel need not obligatorily extend to the surface 112C of the ridge 112A as shown in the sensor embodiment illustrated in FIG. 16. In accordance with other possible embodiments, the level of the gel in the chamber 121 may vary such that the level of the gel is at the level of the surface 112C of the ridge 112A, or, is lower than the level of the surface 112C of the ridge 112A. The gel body 124G may be any of the gels described herein and may be formed or disposed within the open chamber 121 by any of the methods disclosed in detail herein.

Figure 17:
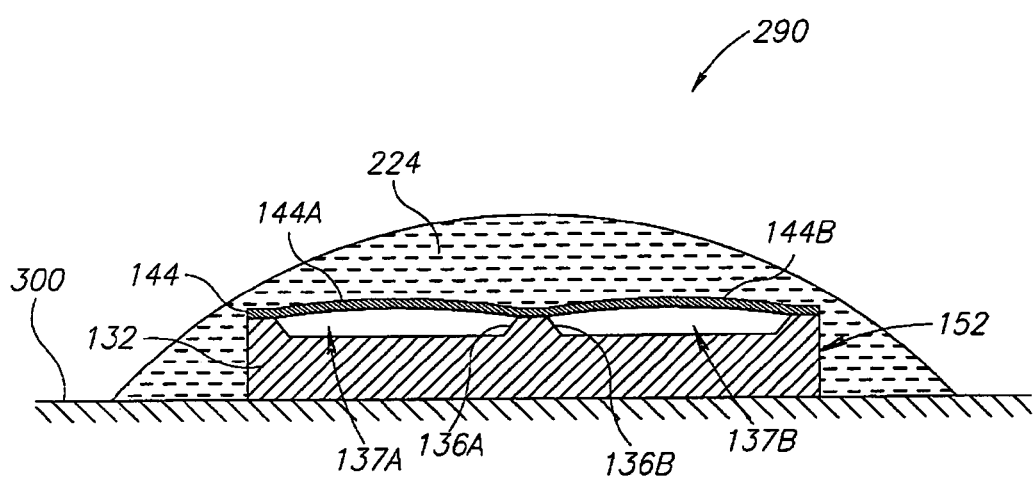
FIG. 17 is a schematic cross-sectional view illustrating a multi-membrane passive ultrasonic pressure sensor completely embedded in a body of protecting gel, in accordance with yet another embodiment of the present invention.

Reference is now made to FIG. 17 which is a schematic cross-sectional view illustrating a multi-membrane passive ultrasonic pressure sensor completely embedded in a body of protecting gel, in accordance with yet another embodiment of the present invention.

The embedded sensor 290 may include the sensor unit 152 disclosed hereinabove (see FIG. 7). The sensor unit 152 may be disposed on or suitably attached to a surface 300 (only a part of the surface 300 is shown in FIG. 17 for the sake of clarity of illustration). The surface 300 may be the surface of an anchor or any other type of sensor carrier or sensor carrying device or sensor positioning device. For example, the surface 300 may be part of a device such as, for example, a sensor-anchoring device, a sensor anchor (such as, but not limited to any of the devices disclosed in U.S. Pat. No. 6,331, 163 to Kaplan), a sensor positioner, an implantable graft, any suitable part of an implantable device, a pacemaker, a defibrillator or a part thereof, an implantable electrode or a part thereof, an insertable electrode or a part thereof, an implantable catheter or a part thereof, an insertable catheter or a part thereof, a stent, a part of a stent, a guide-wire or a part thereof, an endoscopic device or a part thereof, an autonomous or a tethered endoscopic device or a part thereof, an implantable graft or other implant types, or any other suitable device which may be implanted in or inserted into in a body of any organism, animal or human patient.

The surface 300 may also be a surface of a container or any other type of enclosure surrounding or being part of a measurement environment. For example the surface 300 may be a part of the internal surface of the walls of a chemical reactor, or a bioreactor or a tube or any other enclosure or container associated with the measurement environment.

The sensor unit 152 may be attached to the surface 300 by using a suitable glue or by using any other suitable attaching method or suitable attaching material known in the art.

The protected sensor 290 further includes a body of gel 224. The gel 224 may be any of the gels disclosed herein. In accordance with one embodiment of the present invention, the sensor unit 152 may first be suitably attached or glued to the surface 300. After the attachment of the sensor to the surface 300, a suitable amount of the gel precursor or liquefied gel, or a mixture of components capable of forming a gel may be disposed on the sensor unit 152, such that it covers the sensor unit 152 and part of the surface 300. The gel may then be allowed to set, or to solidify or to polymerize as is appropriate. After gel formation or polymerization or setting, the sensor unit 152 may be embedded within resulting body of gel 224.

If the sensor unit 152 is not initially attached or glued to the surface 300, the body of gel 224 may also serve for attaching the sensor unit 152 to the surface 300. In the latter case, the sensor unit may first be placed on the surface 300 at a desired position and a drop or other suitable amount of the gel precursor or liquefied gel, or a mixture of components capable of forming a gel may be disposed on the sensor unit 152, such that it covers the sensor unit 152 and part of the surface 300. The gel may then be allowed to set, or to solidify or to polymerize as is appropriate.

Alternatively, in accordance with another embodiment of the present invention, a drop or other suitable or desired amount of the gel precursor or liquefied gel, or a mixture of components capable of forming a gel may first be disposed at a desired position on the surface 300, the sensor unit 152 may then be placed or immersed within the drop (or the other amount) of gel precursor or liquefied gel, or a mixture of components capable of forming a gel and the gel may then be allowed to set, or to solidify or to polymerize as is appropriate.

It is noted that if the gel 224 is used for attaching the sensor unit 152 to the surface 300, the sensor unit 152 may or may not touch the surface 300 because the sensor unit 152 may be placed such that it is completely surrounded by the body gel 224 without contacting the surface 300. Thus, it is possible to attach the body of gel 224 to the surface 300 while having the sensor unit 152 suspended in the gel 224 without contacting the surface 300.

It is noted that, the disclosed method of embedding one or more sensor units in a gel may have an additional advantage in that it may allow sensor units which are not made of a biocompatible material(s) to be used for implantation in an organism or body, when the gel in which the sensor units are embedded is a biocompatible gel or a hemocompatible gel (for sensor units which may be in contact with blood). Preferably, such a biocompatible or hemocompatible gel is not rapidly degraded or consumed by the components of the measurement environment, and has a sufficient thickness.

It is further noted that the method of embedding a sensor within a body of gel illustrated in FIG. 17 is not limited to being used with a single sensor or a single sensor unit. Rather, multiple sensors or multiple sensor units of any of the types disclosed herein or known in the art may be placed or disposed or embedded within the gel 224 that is attached to the surface 300. This may be advantageous when different types of sensors need to be positioned at the same region of the surface 300 (such as, for example, for forming a temperature compensated sensor pair, or when using multiple sensor units having different resonance frequency ranges, or multiple sensors units for sensing and/or for determining different physical parameters in the measurement environment, or for any other purpose requiring a combination of structurally or functionally similar or different protected sensors placed in the vicinity of each other.

Figure 18:
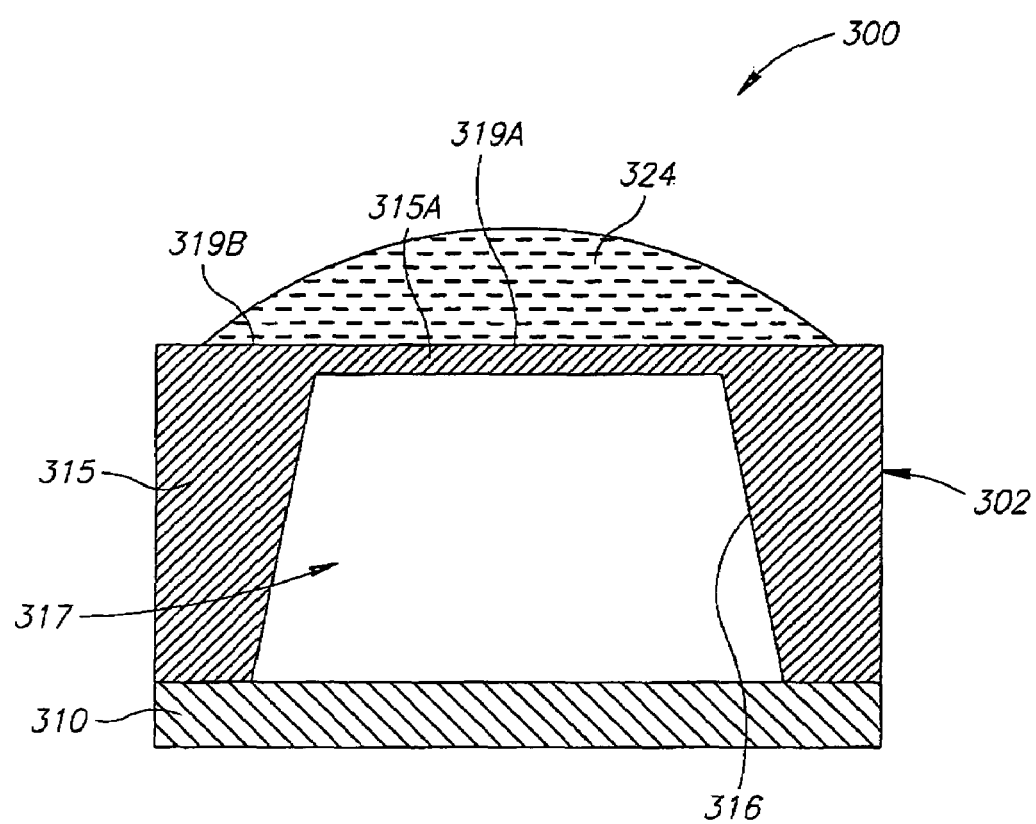
FIG. 18 is a schematic cross-sectional diagram illustrating a gel-protected passive resonating pressure sensor in accordance with another embodiment of the present invention.

Reference is now made to FIG. 18 which is a schematic cross-sectional diagram illustrating a gel-protected passive resonating pressure sensor in accordance with another embodiment of the present invention.

The protected sensor 300 includes a sensor unit 302 and a body of gel 324 attached to the sensor unit 302. The sensor unit 302 includes a recessed substrate 315 having a recess 316 formed therein. The recessed substrate 315 may be, for example a silicon substrate, but may also be made of any other suitable material. The recess 316 may be formed within the substrate 315 using any forming or machining or micromachining method known in the art. For example, if the substrate 315 is made of silicon, the recess 316 may be etched into the substrate 315 using any silicon etching or micromachining method known in the art. Alternatively the substrate 315 may be made of any other suitable material known in the art, such as, but not limited to, a metal, silicon, boron nitride, glass, or the like, as disclosed in detail hereinabove for the substrate layer 12 of the sensor 10.

A second substrate layer 310 may be glued or otherwise sealingly attached to the layer 315 to form a sealed chamber 317 using any suitable attaching method known in the art as is disclosed for sensor 10 or other sensors hereinabove, or as disclosed in U.S. Pat. Nos. 5,989,190 and 6,083,165 to Kaplan. The second substrate layer 310 may be made of any other suitable material known in the art, such as, but not limited to, silicon, metal, boron nitride, glass, or the like, as disclosed in detail hereinabove for the substrate layer 12 of the sensor 10.

The sealed chamber 317 may be evacuated to have vacuum therein by attaching the layer 317 in a vacuum chamber as disclosed hereinabove, or as disclosed in U.S. Pat. Nos. 5,989, 190 and 6,083,165 to Kaplan. Alternatively the sealed chamber may include a gas or gases therein at a suitable pressure level by sealingly attaching the layer 310 to the recessed substrate 315 in a suitable controlled atmosphere pressure chamber, as is known in the art. The thin part of the substrate 315 forms a vibratable membrane 315A that may vibrate when interrogated by a sonic or ultrasonic beam having an appropriate frequency as disclosed in detail hereinabove for the vibratable membranes 14A, 14B and 14C of the sensor 10. The sensor unit 302 may be used for determining the pressure within a measurement environment as disclosed hereinabove in detail for the sensor 10 or any of the other sensor disclosed hereinabove.

The protected sensor 300 may be formed by disposing or attaching the body of gel 324 to the surface portion 319A of the vibratable membrane 315A and to part of the surface 319B of the non-vibratable part of the substrate 315, as is illustrated in FIG. 18. The gel 324 may be formed on or attached to the sensor unit 302 by using any suitable gel forming method, including but not limited to, the methods using a gel precursor or a liquefied gel, or a mixture of components capable of forming a gel by polymerization and/ or cross-linking as disclosed for other sensors described hereinabove. It is noted that the body of gel 324 may cover the entire surface 319A of the vibratable membrane 315A so that it may protect the vibratable membrane 315A from deposition or attachment of extraneous material (not shown) on the surface 319A of the membrane 315A. The body of gel 324 may also cover part of the non-vibratable surface part 319B of the substrate 315 (as is illustrated in FIG. 18). Alternatively, the body of gel 324 may cover the entire surface 319A of the vibratable membrane 315A and all the surface 319B of the non-vibratable thick part of the substrate 315.

Experiment 1

The experiment was performed using the multi-membrane passive ultrasonic pressure sensor 20 illustrated in FIGS. 2 and 3 of co-pending U.S. patent application Ser. No. 10/828, 218 to Girmonski et al. The sensor was first placed on a slab of gelatin. The gelatin slab was prepared from a commercial food grade gelatin powder mixed with warm water (42% w/w) and cast to form a slab having a thickness height) of approximately six centimeters. The gelatin slab was placed in a controlled pressure chamber, and the sensor was positioned on top of the gelatin slab. The gelatin slab and the sensor were then covered with water and interrogated at various different pressure levels by an ultrasonic beam having a carrier frequency at 750 KHz and eleven sensor exciting frequencies of 72 KHz, 74 KHz, 76 KHz, 78 KHz, 80 KHz, 82 KHz, 84 KHz, 86 KHz, 88 KHz, 90 KHz and 92 KHz using the Doppler method disclosed by Girmonsky et al. in the above referenced co-pending U.S. patent application Ser. No. 10/828,218, to obtain a first measurement data set and to determine the resonance frequency of the sensor at each known pressure level in the pressure chamber.

The gelatin slab and the pressure sensor were then taken out of the pressure chamber and placed in a container. A warm solution of commercial food grade gelatin in water (42% w/w) was poured into the container such that it completely covered the sensor and the first gel slab on which the sensor was positioned and was allowed to cool to room temperature to solidify the cast gelatin. The thickness of the gelatin layer covering the sensor was approximately four centimeters. The sensor was thus completely embedded in a block of gelatin, such that the vibratable membranes of the sensor were in contact with and covered by the gelatin. The same series of resonance frequency versus pressure measurements were performed again by placing the resulting block of gelatin with the sensor embedded therein in the same controlled pressure chamber and repeating the measurements of the resonance frequencies for the same experimental pressure levels using the same interrogating ultrasound beam parameters, to obtain a second measurement data set. When the dependence of the sensor's resonance frequency on the pressure level was compared for the first and second sets of measurements, there was no substantial difference between the data set for the bare (non-gelatin covered) sensor and for the same sensor completely embedded in gelatin. This experiment indicates that the sensor used in the experiment may be protected by a gel without substantially affecting the dependence of the resonance frequency of the sensor's vibratable membranes on the external pressure.

Experiment 2

The experiment was performed using the multi-membrane passive ultrasonic pressure sensor 20 illustrated in FIGS. 2 and 3 of co-pending U.S. patent application Ser. No. 10/828, 218 to Girmonski et al. The sensor was first placed in a controlled pressure chamber, covered with water and interrogated at various different pressure levels by an ultrasonic beam, as described for EXPERIMENT 1 above, to obtain a first measurement results data set and to determine the resonance frequency of the sensor at each known pressure level in the pressure chamber. The sensor was then taken out of the water and the upper part of the sensor (including the nine vibratable membranes of the sensor) was then covered with a thin layer of gelatin (42% w/w in water) prepared as disclosed in EXPERIMENT 1 above, by casting the warm gelatin solution on the upper surface of the sensor and letting the gel solidify. The thickness of the gelatin layer covering the upper part of the sensor and covering the vibratable membranes of the sensor was approximately 150 microns. The gel protected sensor was then covered with water and the same series of resonance frequency versus pressure measurements were performed again in the same controlled pressure chamber to obtain a second measurement data set.

When the dependence of the sensor's resonance frequency on the pressure level was compared for the first and second measurements data sets, there was no substantial difference between the data set for the naked (non-gelatin covered) sensor and for the same sensor covered with a thin gelatin layer. This experiment indicates that the sensor used in the experiment, may be protected by a thin layer of gel without substantially affecting the dependence of the resonance frequency of the sensor's vibratable membranes on the external pressure.

It is noted that the various parts and components of the drawing Figures (FIGS. 1-18) are not drawn to scale and the dimensions and shapes are drawn for illustrative purposes only (for the sake of clarity of illustration) and may not represent the actual dimensions of the various illustrated components. For example, the curvature of the vibratable membranes 14A, 14B and 14C of the second layer 14 (of FIG. 1) is greatly exaggerated (for illustrative purposes) relative to the actual curvature of the vibratable membranes of actual sensors.

It is further noted that while the particular examples of the sensors disclosed hereinabove and illustrated in FIGS. 1-18 are adapted for pressure measurements, the protected sensors of the present invention may be also used as temperature sensors as is known in the art and as disclosed hereinabove. It may generally be also possible to use the gel-protected resonating sensors of the present invention for determination of other physical parameters within a measurement environment, if the measured parameters influence the resonance frequency of the vibratable part(s) or vibratable membrane(s) of the sensor. Generally, covering any type of resonating sensor unit(s) with a gel such that at least the resonating parts (such as, but not limited to, resonating members or resonating membranes, or the like) of the sensor unit(s) are covered by the gel, or embedding the resonating sensor unit(s) in a gel may provide protection to the resonating parts of the sensor unit(s) and may prevent accumulation of extraneous material from the measurement environment onto the resonating parts, without substantially affecting the resonance frequency characteristics of the resonating sensor unit(s).

It is further noted that other types of resonating sensors such as the sensors disclosed, inter alia, in U.S. Pat. Nos. 5,619,997, 5,989,190 and 6,083,165 to Kaplan, or any other sensors known in the art, may be implemented as protected sensors by suitable use of a compliant member and a non-compressible medium to form a sealed chamber filled with the non-compressible medium in which the non-compressible medium transmits the physical variable to be measured to the vibratable part of the sensor or to a suitable coupler coupled to the vibratable part.

It will be appreciated by those skilled in the art that the protected sensors of the present invention may be used for determining the value of a physical variable by using various different measurement methods. For example, the resonance frequency of the vibratable part(s) or the vibratable membrane(s) of the protected sensors disclosed hereinabove may be determined by using a continuous beam, or a pulsed beam, or a chirped beam of ultrasound for interrogating the protected sensors of the present invention and by measuring either the absorption of the energy of the exciting beam by the sensor, or the ultrasonic signal emitted by or returned from the sensor as is known in the art. Methods and systems for performing such measurement of the resonance frequency of passive sensors are disclosed in detail in U.S. Pat. Nos. 5,619, 997, 5,989,190 and 6,083,165, and 6,331,163 to Kaplan, and in U.S. patent application Ser. No. 10/828,218, now issued as U.S. Pat. No. 7,134,341, to Girmonski et al.

It is, however, noted that the methods for protecting resonating sensors disclosed hereinabove are not limited for passive ultrasonic sensors disclosed hereinabove or to any particular measurement method disclosed hereinabove, but may be applied to any type of measurement method suitable for use with any type of resonating sensors, such as but not limited to, passive resonating sensors, active resonating sensors, optically interrogated active or passive resonating sensors, capacitive resonating sensors, or any other resonating sensor known in the art which has at least part of its resonating structure exposed to the measurement environment or medium.

It is further noted that during the construction of the protected sensors of the present invention (such as, for example, the sealed chamber 22 of the protected sensor 10) when the sealed chamber is filled with the medium 24 and sealed, care should be taken to avoid the trapping of any bubbles of gas or air in the sealed chamber. While it may still be possible to use a protected sensor containing such bubbles or gas filled spaces for performing measurements (depending, inter alia, on the size and cross-sectional area of such bubbles or gas filed spaces), such bubbles or any amount of gas or air trapped in the non-compressible medium 24 may undesirably affect or degrade the performance of the protected sensor because it introduces a compressible part (the gas in the space or a bubble containing a gas or gases) into the medium in the sealed chamber which may affect the actual pressure experienced by the vibratable membranes (such as, for example, the vibratable membranes 14A, 14B and 14C of the sensor unit 82) of the protected sensor, which may in turn introduce a certain measurement error. Additionally, gas bubbles trapped in the medium 24 contained within the sealed chamber may reflect or scatter part of the interrogating ultrasound beam, which may also undesirably affect the sensor's performance or the measurement system's performance.

Similarly, when constructing the open gel protected or gel covered sensors (such as, but not limited to the sensors illustrated in FIGS. 11-18), care should be taken to avoid or minimize the formation or trapping of gas bubbles within the gel body or bodies or layers protecting the sensors. Such bubbles may reflect or scatter part of the interrogating ultrasound beam, which may undesirably affect the sensor's performance or the measurement system's performance. The formation and trapping of bubbles in the gels may be reduced or avoided by using suitable de-airing or degassing of the pre-gelled liquid or the pre-polymerized gel precursor mixture, as is known in the art, or by using any suitable degassing or de-bubbling method known in the art, for removing existing bubbles or for preventing or reducing bubble formation within the gel.

Furthermore, the protected sensors of the present invention and parts thereof may be constructed of multilayered materials. For example, any of the recessed substrates, spacers, housings, and anchoring devices used in the construction of any of the protected sensors disclosed herein and illustrated in the drawings may (optionally) be formed as a multi-layered structure comprising more than one layer of material. Moreover, if such multi-layered structures are used in a part of the protected sensor, some of the layers may or may not include the same materials.

Moreover, while the examples disclosed hereinabove use certain exemplary gel types for implementing the protected sensors of the invention, many other types of gels may also be used. For example, many other types of gels may be used in implementing the protected sensors of the present invention, such as, but not limited to, polyvinyl alcohol (PVAL) based gels, polyvinylpyrrolidone (PVP) based gels, polyethylene oxide (PEO) based gels, polyvinylmethyl ester (PVME) based gels, polyacrylamide (PAAM) based gels, or any other type of suitable gel, lipogel or hydrogel known in the art.

It is noted that when the selected gel forming method includes the polymerization of a mixture containing suitable gel forming monomers (with or without cross-linking agents), the polymerization may be induced by any suitable method known in the art. For example one possible method of forming a gel is adding a polymerization initiating agent to a solution containing a monomer and (optionally a cross-linking agent). The polymerization initiating agent may be a suitable free-radical forming agent, such as, but not limited to, potassium persulphate in the case of using polyacrylamide forming monomers, or any other suitable polymerization initiating compound known in the art). However, It may also be possible to use other methods for initiating a polymerization of a monomer such as irradiating a suitable monomer solution (with or without suitable cross-linking agents or other copolymers) with light having a suitable wavelength (such as, but not limited ultraviolet light, or light having other suitable wavelengths, or by using other types of ionizing radiation or other types of radiation. However, any other suitable method for initiating polymerization known in the art may be used in forming a gel included in or attached to, or encapsulating the protected sensors of the present invention.

As discussed hereinabove, preferably, the acoustic impedance of the gel should be close to the acoustic impedance of the medium or tissue(s) present in the measurement environment. Additionally, if the gel is to be exposed to the medium in the measurement environment, the composition of the gel should, preferably, be adapted to be compatible with the medium to avoid excessive degradation or decomposition of the gel by the medium in the measurement environment. If the gel-protected sensor is a sensor of the type disclosed in FIGS. 11-18 and is implanted in a body, the gel which may be exposed to the other bodily tissues or blood or other bodily fluids should, preferably, be a biocompatible gel, as is known in the art.

It is further noted that the vibratable members or membranes (or resonating members or membranes) of the sensor units used in the protected sensors of the present invention may have many different shapes and/or geometries. For example, the vibratable membranes of the passive ultrasonic sensor units disclosed hereinabove (such as, but not limited to, the vibratable membranes of the sensors illustrated in FIGS. 1-18) may have a circular shape, a rectangular shape, a polygonal shape, or any other shape known in the art and suitable for a vibratable resonator, as is known in the art.

It will be appreciated by those skilled in the art that the methods disclosed hereinabove for protecting a sensor and for constructing protected sensor are not limited to the various exemplary embodiments disclosed and illustrated herein, and may be applied to other different sensors having vibratable parts or vibratable members or vibratable membranes. For example, the methods disclosed hereinabove may be applied to the compensated passive ultrasonic sensors described in U.S. Pat. Nos. 5,989,190 and 6,083,165 to Kaplan, to construct protected compensated passive ultrasonic sensors that are considered to be within the scope and spirit of the present invention.

It will be appreciated that while the embodiments of the protected resonating sensors and the methods for protecting resonating sensors of the present invention are illustrating as applied to passive resonating sensors, the methods and protected sensors of the present invention may be easily adapted for implementation using active resonating sensors known in the art by modifications and adaptations that may be easily implemented by those skilled in the art. The scope of the present invention therefore also includes protected sensor and methods for protecting sensors applied to any suitable active resonating sensor units known in the art.

It is noted that in all of the protected sensors (with or without a compliant member) disclosed herein it is possible to coat or cover the entire surface of the protected sensor or a part of the sensor (such as, but not limited to, the housing of the sensor and/or the non-vibratable part(s) of a sensor unit or the compliant member of a protected sensor) with a thin layer of material having special desired properties (the covering layer is not shown in the drawing figures for the sake of clarity of illustration). The addition of the covering layer may be done before, during or after the assembling or construction of the sensor, as is appropriate for specific sensor types. When such a covering layer is added on the compliant member the material of the layer should be sufficiently compliant and the covering layer may, preferably, have an acoustic impedance which is close to or equal to the acoustic impedance of the compliant member and/or the medium in the measurement environment.

The covering layer should be sufficiently compliant so as not to impair the sensor's performance. The covering layer may include one or more materials that may have a desired property, or may confer a desired property to any part of the sensor unit or of the protected sensor or may achieve a desirable effect. For example, the covering layer may include one or more hydrophilic materials or hydrophobic materials to confer desired hydrophilic or hydrophobic properties, respectively, to the protected sensor or to a part thereof. Furthermore, the covering layer may include one or more materials that may have desired hydrodynamic surface properties such as but not limited to the resistance (or friction coefficient) to flow of a fluid or liquid in contact with the surface of the coating layer.

Additionally, the covering layer may include one or more materials that may have one or more desired biological properties. For example, such material(s) may affect the growth of biological tissues or cells, as is known in the art. Biological effects may include but are not limited to, induction or inhibition of endothelial cell growth (or endothelial cell monolayer growth), affecting blood clot formation, inhibiting or promoting blood cell deposition and/or adhesion, or any other desirable biological effect(s) known in the art.

Alternatively or additionally, the present invention also includes modifying the surface properties of the compliant member(s) of the protected sensor, or the surface of the body of gel in the open protected gels of the present invention, or of any other surface of any other part of the protected sensor (such as, but not limited to, the housing of the sensor, or a sensor anchor, or a spacer, or the like), using any suitable surface treatment or surface modification method known in the art, useful for changing the surface properties of the protected sensor or a part thereof. Such methods may include any chemical methods and/or physical methods for modifying a surface, as is known in the art. For example the protected sensor or any part(s) thereof may be treated chemically to change their surface properties, including but not limited to chemical surface properties, surface hydrophobicity, surface hydrophilicity, rheological surface properties, biological surface properties, surface resistance to deposition of cells or tissues thereon, or the like. The chemical treatment may be achieved by either chemically modifying surface chemical groups of the surface as is known in the art (such as, for example sillanization of surface hydroxyl groups), or by suitably attaching various different chemical molecules or biological molecules to the surface (with or without using linking molecules or agents). Such molecules or agents may include, but are not limited to, proteins, peptides, drugs, polysaccharides, lipids, glycolipids, lipoproteins, glycoproteins, proteoglycans, extracellular matrix components, nucleic acids, polynucleotides, RNA, DNA, anti-sense nucleic acid sequences, receptors, enzymes, antibodies, antigens, enzyme inhibitors, cell proliferation inhibitors, growth regulating factors, growth inhibiting factors, growth promoting factors, anti-coagulant agents, anti-clotting agents, tumor inhibiting drugs, tumor inhibiting factors, tumor suppressing agents, anti-cancer drugs, or any other type of molecule or factor or drug or agent having a desired biological or therapeutic property or effect, as is known in the art. Any suitable method known in the art may be used for performing such surface derivatization or surface modification or surface treatment, or surface attachment of agents or molecules, to any desired surface of the protected sensors of the present invention. Such methods for treating and/or modifying surfaces are well known in the art and will therefore not be discussed in details hereinafter.

It is noted that if the body of gel is treated to modify it's surface properties, care should be taken to ensure that the gel treatment or chemical modification that is used for modifying the surface properties of the protecting body of gel does not substantially change the properties of the gel that ensure proper transmission of the measured physical variable (such as, but not limited to the pressure in the measurement environment) through the body of gel, or the acoustic impedance of the gel, and does not adversely affect the performance of the protected sensor.

In accordance with an additional embodiment of the present invention, the body of gel of the protected sensors of the invention may function as a reservoir for releasing a desired substance. The body of gel (including, but not limited to, the bodies of gel 124, 124A, 124B, 124C, 124G, 224 and 324) may include one or more substances which may include, but are not limited to, proteins, peptides, different drugs or therapeutic agents, polysaccharides, lipids, glycolipids, lipoproteins, glycoproteins, proteoglycans, extracellular matrix components, nucleic acids, polynucleotides, RNA, DNA, anti-sense nucleic acid sequences, receptors, enzynes, antibodies, antigens, enzyme inhibitors, cell proliferation inhibitors, growth regulating factors, growth inhibiting factors, growth promoting factors, anti-coagulant agents, anti-clotting agents, tumor inhibiting drugs, tumor inhibiting factors, tumor suppressing agents, anti-cancer drugs, or any other type of molecule or factor or drug or agent having a desired biological or therapeutic property or effect, as is known in the art. Such substances may be introduced into the body of gel before the gel is disposed in or applied to the protected sensor by introducing the substance(s) into the gel or the gel forming liquid at the stage preparing the gel. Alternatively, the substance(s) may be introduced into the body of gel after the gel is placed in or disposed on the protected sensor. For example, the desired substance(s) may be introduced into the body gel by placing the protected sensor in a suitable solution containing the substance(s). The substance(s) may then enter the body of gel by diffusion.

The body of gel may thus operate as a substance(s) reservoir when implanted in a body or an organism and may release the substance(s) into the blood (if implanted in a part of a cardiovascular system) or into any other body fluids or interstitial fluid depending on the site of implantation of the sensor. The release of such substance(s) may be advantageous by affecting the growth of biological tissues or cells, as is known in the art. Effects of the released substance(s) may include but are not limited to, induction or inhibition of endothelial cell growth (or endothelial cell monolayer growth), affecting blood clot formation, inhibiting or promoting blood cell deposition and/or adhesion, or any other desirable biological effect(s) known in the art. Such effects may reduce or prevent deposition of blood cells or other substances or tissues on the gel. Additionally, the release of the substance(s) or drugs from the gel may also have a desired therapeutic effect on tissues, cells or other targets in the vicinity of the sensor, irrespective of their efficacy in reducing cell or tissue deposition on the gel. For example, suitable drugs or substances released from the gel of an ultrasonic protected pressure sensor implanted in a coronary artery may reduce atherosclerotic plaque formation in the coronary blood vessel. Other drugs or substances may induce other desired therapeutic effects at or near the site of implantation of the sensor, as is known in the pharmaceutical art. It is noted that the type of gel used in the protected sensor may affect the type of substance(s) or drugs that may be included and effectively released from the gel. For example a suitable lipogel or hydrophobic gel may be used for storing and releasing lipophilic or hydrophobic substances or drugs, while a hydrogel may be used to store and release hydrophilic or polar substances or drugs. Thus different types of gels may be selected to store and release different types of drugs and substances.

The composition and properties of the protecting gel may also be selected to reduce or inhibit the diffusion of proteins (such as, inter alia, collagen) or other substances (for example, substances included in the measurement environment in a reactor or bioreactor, or the like) into the body of gel protecting the sensor(s) and their possible deposition onto the vibratable member(s) or membrane(s) of the sensor unit(s). Such properties may include, inter alia, the gel's porosity, the molecular sieve properties and degree of cross-linking, the presence of ionizable groups or electrically charged groups or polar groups or apolar groups or hydrophobic groups in the gel's chemical composition, the gel's hydrophobic properties, or any other gel property which may desirably reduce or prevent the ability of proteins or other substances or molecules to diffuse into the gel and to eventually be deposited on the vibratable sensor parts. For example, lipophilic gel compositions may retard or reduce the diffusion of collagen (and/or other proteins or substances) through the gel and its deposition on the vibratable sensor parts, but other different gel types or compositions may also be used Additionally, the gel may also be used as a reservoir of suitable substance(s) or agents or molecules which may be incorporated into the gel using any of the methods disclosed hereinabove and known in the art, and which may retard or reduce the diffusion of collagen (and/or other proteins or substances) through the gel and its deposition on the vibratable sensor parts. Such substances may function, inter alia, by changing the properties of the gel upon being incorporated or introduced into the gel. When selecting the gel's composition or adding or incorporating substances to the gel to retard or reduce diffusion and deposition of foreign substances, it should be born in mind that the acoustic impedance of the selected gel composition should, preferably (but not obligatorily), be close to or equal to the acoustic impedance of the medium in measurement environment, as explained in detail hereinabove.

It is noted that the body of gel protecting the vibratable members or parts of the resonating sensors need not necessarily be a single contiguous body of gel but may also comprise several non contiguous bodies of gel (as is shown in detail in FIGS. 7 and 15). Moreover, in accordance with other embodiment of the present invention, more than one body of gel may be used in a single protected sensor. For example, in the sensor 260 of FIG. 14, it may be possible to attach a separate block of gel (not shown in FIG. 14) to each of the vibratable membranes 14A, 14B and 14C. Similarly, in the protected sensor 250 of FIG. 13 it may be possible to replace the single body of gel 252 by two non-contiguous bodies of gel (not shown), such that a first body of gel (not shown) is attached to the sensor unit 55 and the second body of gel (not shown) is attached to the sensor unit 57. Similarly, turning briefly to FIG. 17, the body of gel 224 may be replaced with two bodies of gel (not shown) each suitably attached to one of the vibratable membranes 144A and 144B. The protected sensor 290 (of FIG. 17) may also be modified by embedding two or more separate sensor units (not shown) in the body of gel 224 instead of the single embedded sensor unit 152. Similar permutations and modifications may be similarly used for any of the protected sensors disclosed hereinabove and illustrated in the drawing figures. These permutations and modifications are considered to be within the scope and spirit of the present invention.

While the invention has been described with respect to a limited number of embodiments, it will be appreciated that many variations, permutations and modifications may be made to the structure, dimensions, material composition, number and shape of the resonating members, number and/or shape of bodies of gel per protected sensor or per sensor unit, and construction methods of the protected sensors of the present invention, and other numerous applications of the protected sensors of the present invention which are all considered to be within the scope and spirit of the present invention.

The invention claimed is:

1. A protected resonating sensor comprising:
   one or more resonating sensor units, each sensor unit of said one or more resonating sensor units has at least one vibratable member having a resonance frequency that varies as a function of a physical variable in a measurement environment, said at least one vibratable member is configured for being excited by an ultrasonic beam directed at said one or more sensor units and for returning an ultrasonic signal receivable by an ultrasonic receiver disposed outside of said measurement environment; and
   at least one body of gel in contact with said at least one vibratable member of said one or more resonating sensor units.

2. The protected sensor according to claim 1 wherein said gel has an acoustic impedance and the acoustic impedance of said at least one body of gel is close to or equal to the acoustic impedance of a medium disposed in said measurement environment.

3. The protected sensor according to claim 1 wherein said protected sensor is an implantable sensor configured to be implanted in a body or organism, and wherein the acoustic impedance of said at least one body of gel is close to or equal to the acoustic impedance of one or more tissues of said body or organism.

4. The protected sensor according to claim 1 wherein said one or more resonating sensor units are embedded in said at least one body of gel.

5. The protected sensor according to claim 1 wherein said at least one body of gel completely covers all the vibratable members included in said one or more resonating sensor units.

6. The protected sensor according to claim 1 wherein said at least one body of gel is selected from a synthetic gel, a natural gel, a hydrogel, a lipogel, a hydrophobic gel, a hydrophilic gel, a biocompatible gel, a hemocompatible gel, a polymer based gel, a cross-linked polymer based gel and combinations thereof.

7. The protected sensor according to claim 1 wherein said protected sensor further includes a housing.

8. The protected sensor according to claim 7 wherein said at least one body of gel at least partially fills said housing.

9. The protected sensor according to claim 1 wherein said at least one body of gel comprises at least one thin layer of gel attached to said at least one vibratable member of said one or more resonating sensor units.

10. The protected sensor according to claim 1 wherein said one or more resonating sensor units are disposed within at least one open chamber.

11. The protected sensor according to claim 10 wherein said at least one chamber is selected from, at least one chamber formed within a sensor anchoring device, and at least one chamber comprising part of a sensor anchoring device.

12. The protected sensor according to claim 11 wherein said sensor anchoring device is selected from a sensor anchor, a sensor positioner, an implantable graft, a sensor fixating device, an implant, an implantable device, an implantable graft, a part of an implantable device, a pacemaker, a part of a pacemaker, a defibrillator, a part of a defibrillator, an implantable electrode, an insertable electrode, an endoscopic device, a part of an endoscopic device, an autonomous endoscopic device, a part of an autonomous endoscopic device, a tethered endoscopic device, a part of a tethered endoscopic device, an implantable catheter, an insertable catheter, a stent, a part of a stent, a guide-wire, a part of a guide-wire, an implantable therapeutic substance releasing device, and an insertable therapeutic substance releasing device.

13. The protected sensor according to claim 1 wherein said at least one resonating sensor unit is selected from a passive sensor unit, an active sensor unit, a passive resonating sensor unit, an active resonating sensor unit, a pressure sensor, a passive ultrasonic pressure sensor, an active ultrasonic pressure sensor, and a sensor for sensing the concentration of a chemical species in a measurement environment.

14. The protected sensor according to claim 1 wherein at least one resonating sensor unit of said one or more resonating sensor units comprises, a substrate having one or more recesses formed therein, and a second layer sealingly attached to said substrate to form one or more sealed sensor unit chambers within said at least one resonating sensor unit.

15. The protected sensor according to claim 14 wherein said at least one vibratable member of said at least one resonating sensor unit is selected from, at least one vibratable member comprising a portion of said substrate, and at least one vibratable member comprising a portion of said second layer overlying said one or more recesses.

16. The protected sensor according to claim 14 wherein each sealed sensor unit chamber of said one or more sealed sensor unit chambers has a pressure level therewithin.

17. The protected sensor according to claim 16 wherein said pressure level is selected from a zero pressure level and a non-zero pressure level.

18. The protected sensor according to claim 16 wherein said protected sensor comprises a first resonating sensor unit having one or more sealed sensor unit chambers and at least a second resonating sensor unit having one or more sealed sensor unit chambers, and wherein the pressure level within at least one sealed sensor unit chamber of said first resonating sensor unit is different than the pressure level within at least one sealed sensor unit chamber of said at least second resonating sensor unit.

19. The protected sensor according to claim 1 wherein said one or more resonating sensor units are selected from, at least one passive ultrasonic pressure sensor unit having a single vibratable membrane, and at least one passive ultrasonic pressure sensor unit having multiple vibratable membranes.

20. The protected sensor according to claim 1 wherein said protected sensor is an implantable protected sensor.

21. The protected sensor according to claim 20 wherein one or more of the components of said implantable protected sensor comprises one or more materials selected from biocompatible materials and hemocompatible materials.

22. The protected sensor according to claim 20 wherein said protected sensor is configured for implantation within a measurement environment selected from, an eye, a urether, a cardiac chamber, a cardiovascular system, a part of a cardiovascular system, an annurismal sac after endovascular repair, a spine, an intervertebral disc, a spinal cord, a spinal column, an intracranial compartment, an intraluminal space of a blood vessel, an artery, a vein, an aorta, a pulmonary blood vessel, a carotid blood vessel, a brain blood vessel, and a coronary artery, a femoral artery, an iliac artery, a hepatic artery, a renal artery and a vena cava.

23. The protected sensor according to claim 1 wherein at least part of the surface of said protected sensor is a modified surface having modified surface properties.

24. The protected sensor according to claim 23 wherein said modified surface properties are selected from physical surface properties, chemical surface properties, electrochemical surface properties, biological surface properties, surface resistance to deposition of cells or tissues thereon, rheological surface properties, and any combinations thereof.

25. The protected sensor according to claim 23 wherein said modified surface is a chemically treated surface.

26. The protected sensor according to claim 23 wherein said protected sensor also includes at least one non-resonating sensor unit.

27. The protected sensor according to claim 23 wherein said modified surface is a surface of said at least one body of gel.

28. The protected sensor according to claim 1 wherein said at least one body of gel comprises at least one releasable substance.

29. The protected sensor according to claim 28 wherein said at least one releasable substance is selected from the group consisting of a protein, a peptide, a drug, a therapeutic agent, a polysaccharide, a lipid, a glycolipid, a lipoprotein, a glycoprotein, a proteoglycans, an extracellular matrix component, a nucleic acid, a polynucleotide, RNA, DNA, an anti-sense nucleic acid sequence, a receptor, an enzyme, an antibody, an antigen, an enzyme inhibitor, a cell proliferation inhibitor, a growth regulating factor, a growth inhibiting factor, a growth promoting factor, an anti-coagulant agent, an anti-clotting agent, a tumor inhibiting drug, a tumor inhibiting factor, a tumor suppressing agent, an anti-cancer drug, and any combinations thereof.

30. The protected sensor according to claim 1 wherein said at least one body of gel comprises a substantially non-compressible gel.

31. The protected sensor according to claim 1 wherein said at least one body of gel comprises a gel having a composition capable of retarding or reducing the diffusion of one or more substances into said gel.

32. The protected sensor according to claim 1 wherein said at least one body of gel comprises a gel having a composition capable of retarding or reducing the deposition of one or more substances onto said at least one vibratable member of said one or more resonating sensor units.

33. A protected sensor comprising at least one resonating sensor unit, each sensor unit of said at least one resonating sensor unit has at least one vibratable member having a resonance frequency that varies as a function of a physical variable in a measurement environment, said at least one vibratable member is configured for being excited by an ultrasonic beam directed at said at least one resonating sensor unit and for returning an ultrasonic signal receivable by an ultrasonic receiver disposed outside of said measurement environment wherein at least one vibratable member of said at least one resonating sensor unit is protected by a gel attached thereto.

34. A method for constructing a protected a resonating sensor the method comprising the steps of:
providing one or more resonating sensor units, each sensor unit of said one or more resonating sensor units has at least one vibratable member having a resonance frequency that varies as a function of a physical variable in a measurement environment said at least one vibratable member is configured for being excited by an ultrasonic beam directed at said one or more sensor units and for returning an ultrasonic signal receivable by an ultrasonic receiver disposed outside of said measurement environment; and
attaching at least one body of gel to said one or more resonating sensor units.

35. The method according to claim 34 wherein said step of attaching comprises covering all the vibratable members of said one or more resonating sensor units with said gel.

36. The method according to claim 34 wherein said step of attaching comprises,
applying a liquefied gel to cover at least all the vibratable members of said one or more resonating sensor units with said liquefied gel, and
allowing said liquefied gel to solidify.

37. The method according to claim 36 wherein said liquefied gel is obtained by heating a liquefiable gel.

38. The method according to claim 34 wherein said step of attaching comprises,
applying a liquid comprising at least one gel precursor to cover at least all the vibratable members of said one or more resonating sensor units with said liquid, and
allowing said at least one body of gel to form from said liquid.

39. The method according to claim 34 wherein said at least one gel precursor comprise at least one monomer capable of being polymerized to form said at least one body of gel.

40. The method according to claim 34 wherein said step of attaching comprises embedding said one or more resonating sensor units within said at least one body of gel.

41. The method according to claim 34 wherein said step of attaching comprises completely embedding or partially embedding said one or more resonating sensor units in said at least one body of gel wherein said at least one body of gel is attached to a surface.

42. The method according to claim 41 wherein said surface is selected from, a surface of a sensor housing, a surface of a sensor anchoring device, a surface of an implantable graft, a surface of an implantable device, a surface of an implant, a surface of an insertable device, and a surface of an enclosure surrounding a measurement environment.

43. The method according to claim 34 wherein said body of gel has an acoustic impedance, said acoustic impedance of said body of gel is close to or equal to the acoustic impedance of a medium contained in a measurement environment in which said protected sensor is disposed.

44. The method according to claim 34 wherein said protected sensor is an implantable protected sensor configured for implantation within an organism, and wherein the acoustic impedance of said gel is close to or equal to the acoustic impedance of at least one tissue or bodily fluid of said organism.

45. The method according to claim 34 wherein said step of attaching comprises,
disposing said one or more resonating sensor units in a housing,
at least partially filling said housing with a liquid comprising at least one gel precursor to cover at least a vibratable member of said one or more resonating sensor units with said liquid, and
allowing said at least one body of gel to form from said liquid.

46. The method according to claim 34 wherein said protected resonating sensor further comprises at least one non-resonating sensor unit, and wherein said step of attaching comprises attaching said at least one non-resonating sensor unit to said at least one body of gel.

47. The method according to claim 34 further including the step of treating at least part of the surface of said protected sensor for modifying the surface properties of said at least part of said protected sensor.

48. The method according to claim 47 wherein said step of treating is performed on said at least one body of gel to change the surface properties thereof.

49. The method according to claim 47 wherein said surface properties are selected from physical surface properties, chemical surface properties, electrochemical surface properties, biological surface properties, surface resistance to deposition of cells or tissues thereon, rheological surface properties, and any combinations thereof.

50. The method according to claim 47 wherein said step of treating comprises chemically treating said at least part of the surface of said protected sensor for modifying the surface properties thereof.

51. The method according to claim 34 further including the step of incorporating at least one releasable substance in said at least one body of gel.

52. The method according to claim 51 wherein said at least one releasable substance is selected from the group consisting of a protein, a peptide, a drug, a therapeutic agent, a polysaccharide, a lipid, a glycolipid, a lipoprotein, a glycoprotein, a proteoglycans, an extracellular matrix component, a nucleic acid, a polynucleotide, RNA, DNA, an anti-sense nucleic acid sequence, a receptor, an enzyme, an antibody, an antigen, an enzyme inhibitor, a cell proliferation inhibitor, a growth regulating factor, a growth inhibiting factor, a growth promoting factor, an anti-coagulant agent, an anti-clotting agent, a tumor inhibiting drug, a tumor inhibiting factor, a tumor suppressing agent, an anti-cancer drug, and any combinations thereof.

53. The method according to claim 51 wherein said step of incorporating comprises adding said at least one releasable substance to said gel prior to disposing said gel in said protected sensor.

54. The method according to claim 53 wherein said step of adding is selected from, adding said at least one releasable substance to a liquid gel precursor, and adding said at least one releasable substance to a liquefied gel.

55. The method according to claim 51 wherein said step of incorporating comprises introducing said at least one releasable substance to said gel after disposing said gel in said protected sensor.

56. The method according to claim 55 wherein said step of introducing comprises diffusing said at least one releasable substance into said at least one body of gel.

57. The method according to claim 56 wherein said diffusing comprises incubating said protected sensor in a solution comprising said at least one releasable substance.

58. A method for constructing a protected a resonating sensor, the method comprising the steps of:
providing one or more resonating sensor units, each sensor unit of said one or more resonating sensor units has at least one vibratable member having a resonance frequency that varies as a function of a physical variable in a measurement environment said at least one vibratable member is configured for being excited by an ultrasonic beam directed at said one or more sensor units and for returning an ultrasonic signal receivable by an ultrasonic receiver disposed outside of said measurement environment; and covering said at least one vibratable member of said one or more resonating sensor units with a gel.

59. A method for constructing a protected a resonating sensor, the method comprising the steps of:

providing one or more resonating sensor units, each sensor unit of said one or more resonating sensor units has at least one vibratable member having a resonance frequency that varies as a function of a physical variable in a measurement environment said at least one vibratable member is configured for being excited by an ultrasonic beam directed at said one or more sensor units and for returning an ultrasonic signal receivable by an ultrasonic receiver disposed outside of said measurement environment; and providing a gel in contact with said at least one vibratable member of said one or more resonating sensor units.

60. A method for protecting a resonating sensor unit having one or more vibratable members, said one or more vibratable members are configured for being excited by an ultrasonic beam directed at said resonating sensor unit and for returning an ultrasonic signal receivable by an ultrasonic receiver disposed outside of said measurement environment, the method comprises the step of covering at least said one or more vibratable members of said sensor unit with a gel.

61. A method for protecting a resonating sensor unit having one or more vibratable members said one or more vibratable members are configured for being excited by an ultrasonic beam directed at said resonating sensor unit and for returning an ultrasonic signal receivable by an ultrasonic receiver disposed outside of said measurement environment, the method comprises the step of covering at least one vibratable member of said sensor unit with a gel.

* * * * *